(12) United States Patent
Leak et al.

(10) Patent No.: US 6,994,698 B2
(45) Date of Patent: Feb. 7, 2006

(54) FLEXIBLE MECHANICAL FASTENING TAB

(75) Inventors: A. Todd Leak, Neenah, WI (US);
Apiromraj Srisopark Roslansky, Little Chute, WI (US); Paul Theodore Van Gompel, Hortonville, WI (US); Georgia Lynn Zehner, Larsen, WI (US); Edward Herman Ruscher, Appleton, WI (US); Yung Hsiang Huang, Appleton, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 0 days.

(21) Appl. No.: 08/366,090

(22) Filed: Dec. 28, 1994

(65) Prior Publication Data

US 2003/0100878 A1  May 29, 2003

(51) Int. Cl.
*A61F 13/15* (2006.01)

(52) U.S. Cl. .................................... 604/391
(58) Field of Classification Search ............... 604/385.1
See application file for complete search history.

(56) References Cited

U.S. PATENT DOCUMENTS

| | | | |
|---|---|---|---|
| 2,511,406 A | 6/1950 | Israel | 128/284 |
| 2,524,842 A | 10/1950 | Slamon et al. | 154/41 |
| 2,649,858 A | 8/1953 | Le Bolt | 128/287 |
| 2,936,758 A | 5/1960 | Csulits | 128/284 |
| 3,081,772 A | 3/1963 | Brooks et al. | 128/287 |
| 3,110,312 A | 11/1963 | Wirth | 128/287 |
| 3,138,841 A | 6/1964 | Naimer | 24/204 |
| 3,141,461 A | 7/1964 | Farris | 128/284 |
| 3,146,778 A | 9/1964 | Krawiec | 128/349 |
| 3,147,528 A | 9/1964 | Erb | 24/204 |
| 3,150,664 A | 9/1964 | Noel | 128/287 |
| 3,180,335 A | 4/1965 | Duncan et al. | 128/287 |
| 3,196,511 A | 7/1965 | Kintner | 24/204 |
| 3,315,676 A | 4/1967 | Cooper | 128/287 |
| 3,318,632 A | 5/1967 | Struble et al. | 297/220 |
| 3,359,980 A | 12/1967 | Rosenblatt | 128/284 |
| 3,490,107 A | 1/1970 | Brumlik | 24/204 |
| 3,494,006 A | 2/1970 | Brumlik | 24/204 |
| 3,497,925 A | 3/1970 | Brumlik | 24/204 |
| 3,550,223 A | 12/1970 | Erb | 24/204 |
| 3,559,648 A | 2/1971 | Mason, Jr. | 128/287 |

(Continued)

FOREIGN PATENT DOCUMENTS

| | | |
|---|---|---|
| AU | 74/74625 | 10/1974 |
| BE | 76 18 87 | 1/1971 |
| BE | 848690 | 3/1977 |

(Continued)

OTHER PUBLICATIONS

Decision revoking EP 0800379 from European Patent Office dated Nov. 29, 2002, 26 pages.
Translation of a further submission by Koester GmbH & Co. KG in the Opposition to European Patent 0 800 379 B1.

(Continued)

*Primary Examiner*—Vy Bui
(74) *Attorney, Agent, or Firm*—Thomas J. Mielke; Alyssa A. Dudkowski; John L. Brodersen

(57) ABSTRACT

Disclosed is a mechanical fastening tab formed from a substrate adapted to be joined to a disposable absorbent product and a first mechanical fastener component. The fastening tab has a Gurley stiffness value of less than about 1000 milligrams in an area of the fastening tab which includes said first mechanical fastening component. Also disclosed are disposable products comprising such mechanical fastening tabs.

42 Claims, 8 Drawing Sheets

U.S. PATENT DOCUMENTS

| | | |
|---|---|---|
| 3,562,770 A | 2/1971 | Erb .................... 24/204 |
| 3,572,342 A | 3/1971 | Lindquist et al. ............ 128/287 |
| 3,594,873 A | 7/1971 | Hockmeyer, Jr. et al. ..... 24/204 |
| 3,599,640 A | 8/1971 | Larson .................... 128/286 |
| 3,618,608 A | 11/1971 | Brink .................... 128/287 |
| 3,620,217 A | 11/1971 | Gellert .................... 128/284 |
| 3,630,201 A | 12/1971 | Endres .................... 128/287 |
| 3,653,381 A | 4/1972 | Warnken .................... 128/284 |
| 3,673,301 A | 6/1972 | Billarant .................... 264/163 |
| 3,686,718 A | 8/1972 | Brumlik .................... 24/204 |
| 3,694,867 A | 10/1972 | Stumpf .................... 24/204 |
| 3,710,425 A | 1/1973 | Brumlik .................... 24/204 |
| 3,778,870 A | 12/1973 | Bennett .................... 24/204 R |
| 3,779,246 A | 12/1973 | Mesek et al. ................ 128/287 |
| 3,800,796 A | 4/1974 | Jacob .................... 128/284 |
| 3,825,006 A | 7/1974 | Ralph .................... 128/287 |
| 3,840,945 A | 10/1974 | Brumlik .................... 24/204 |
| 3,848,594 A | 11/1974 | Buell .................... 128/284 |
| 3,860,003 A | 1/1975 | Buell .................... 604/385.2 |
| 3,863,304 A | 2/1975 | Brumlik .................... 24/204 |
| 3,869,761 A | 3/1975 | Schaar .................... 24/73 VA |
| 3,879,835 A | 4/1975 | Brumlik .................... 29/412 |
| 3,882,871 A | 5/1975 | Taniguchi .................... 128/287 |
| 3,889,322 A | 6/1975 | Brumlik .................... 24/204 |
| 3,899,803 A | 8/1975 | Brumlik .................... 24/204 |
| 3,900,652 A | 8/1975 | Uraya et al. .................... 428/92 |
| 3,905,071 A | 9/1975 | Brumlik .................... 24/204 |
| 3,913,183 A | 10/1975 | Brumlik .................... 24/204 |
| 3,920,018 A | 11/1975 | Schaar .................... 128/287 |
| 3,921,258 A | 11/1975 | Brumlik .................... 24/204 |
| 3,922,455 A | 11/1975 | Brumlik .................... 428/85 |
| 3,927,674 A | 12/1975 | Schaar .................... 128/287 |
| 3,931,666 A | 1/1976 | Karami .................... 24/73 VA |
| 3,950,824 A | 4/1976 | Karami .................... 24/67 AR |
| 3,955,575 A | 5/1976 | Okuda .................... 128/284 |
| 3,963,029 A | 6/1976 | Brooks .................... 128/287 |
| 3,989,048 A | 11/1976 | Cepuritis et al. ............ 128/287 |
| 4,005,712 A | 2/1977 | Karami .................... 128/284 |
| 4,014,340 A | 3/1977 | Cheslow .................... 128/287 |
| 4,022,210 A | 5/1977 | Glassman .................... 128/284 |
| 4,036,233 A | 7/1977 | Kozak .................... 128/287 |
| 4,047,530 A | 9/1977 | Karami .................... 128/287 |
| 4,049,001 A | 9/1977 | Tritsch .................... 128/287 |
| 4,050,463 A | 9/1977 | Schaar .................... 128/287 |
| 4,051,854 A | 10/1977 | Aaron .................... 128/284 |
| 4,056,281 A | 11/1977 | Byrnes .................... 297/220 |
| 4,074,397 A | 2/1978 | Rosin .................... 24/73 AS |
| 4,081,301 A | 3/1978 | Buell .................... 156/164 |
| 4,114,621 A | 9/1978 | Mims, Jr. .................... 128/288 |
| 4,127,132 A | 11/1978 | Karami .................... 128/287 |
| 4,158,906 A | 6/1979 | Watson .................... 24/83 |
| 4,166,464 A | 9/1979 | Korpman .................... 128/287 |
| 4,169,303 A | 10/1979 | Lemelson .................... 24/204 |
| 4,180,890 A | 1/1980 | Brumlik .................... 24/204 |
| 4,205,679 A | 6/1980 | Repke et al. ................ 128/287 |
| 4,229,835 A | 10/1980 | Shaw .................... 2/406 |
| 4,230,113 A | 10/1980 | Mehta .................... 128/287 |
| 4,237,889 A | 12/1980 | Gobran |
| 4,241,462 A | 12/1980 | Tagawa et al. ................ 2/406 |
| 4,259,957 A | 4/1981 | Sonenstein et al. ......... 128/287 |
| 4,290,174 A | 9/1981 | Kalleberg .................... 24/204 |
| 4,296,750 A * | 10/1981 | Woon .................... 604/390 |
| 4,299,223 A | 11/1981 | Cronkrite .................... 128/287 |
| 4,315,508 A | 2/1982 | Bolick .................... 604/392 |
| 4,322,875 A | 4/1982 | Brown et al. .................... 24/204 |
| 4,338,939 A | 7/1982 | Daville .................... 128/286 |
| 4,352,355 A | 10/1982 | Mesek et al. ................ 128/287 |
| 4,380,450 A | 4/1983 | Reich .................... 604/386 |
| 4,381,781 A | 5/1983 | Sciaraffa et al. ............ 604/372 |
| 4,388,075 A | 6/1983 | Mesek et al. ................ 604/385 |
| 4,397,645 A | 8/1983 | Buell .................... 604/380 |
| 4,402,690 A | 9/1983 | Redfern .................... 604/391 |
| 4,410,327 A | 10/1983 | Baggaley .................... 604/391 |
| 4,425,128 A | 1/1984 | Motomura .................... 604/381 |
| 4,430,086 A | 2/1984 | Repke .................... 604/385 |
| 4,463,486 A | 8/1984 | Matsuda .................... 28/161 |
| 4,475,912 A | 10/1984 | Coates .................... 604/385 |
| 4,509,512 A | 4/1985 | LeClercq .................... 128/160 |
| 4,522,874 A | 6/1985 | Pommez .................... 428/284 |
| 4,537,591 A | 8/1985 | Coates .................... 604/391 |
| 4,541,154 A | 9/1985 | Ito et al. .................... 24/442 |
| 4,560,381 A | 12/1985 | Southwell .................... 604/396 |
| 4,568,342 A | 2/1986 | Davis .................... 604/391 |
| 4,568,344 A | 2/1986 | Suzuki et al. ................ 604/389 |
| 4,573,986 A | 3/1986 | Minetola et al. ............ 604/366 |
| 4,576,599 A | 3/1986 | Lipner .................... 604/390 |
| 4,576,601 A | 3/1986 | Brain .................... 604/398 |
| 4,577,591 A | 3/1986 | Wesseldine .................... 119/143 |
| 4,578,066 A | 3/1986 | O'Connor .................... 604/366 |
| 4,581,772 A | 4/1986 | Smith .................... 2/111 |
| 4,585,450 A | 4/1986 | Rosch et al. ................ 604/390 |
| 4,596,568 A | 6/1986 | Flug .................... 604/369 |
| 4,604,096 A | 8/1986 | Dean et al. ............. 604/385 A |
| 4,609,581 A | 9/1986 | Ott .................... 428/100 |
| 4,610,678 A | 9/1986 | Weisman et al. ............ 604/368 |
| 4,610,680 A | 9/1986 | LaFleur .................... 604/385 A |
| 4,610,682 A | 9/1986 | Kopp .................... 604/385 R |
| 4,615,695 A | 10/1986 | Cooper .................... 604/385 A |
| 4,617,022 A | 10/1986 | Pigneul et al. ............. 604/391 |
| 4,623,339 A | 11/1986 | Ciraldo et al. ............. 604/359 |
| 4,626,305 A | 12/1986 | Suzuki et al. ................ 156/164 |
| 4,636,207 A | 1/1987 | Buell .................... 604/370 |
| 4,639,949 A | 2/1987 | Ales et al. .................... 2/400 |
| 4,642,110 A | 2/1987 | Dudek .................... 604/385.1 |
| 4,642,819 A | 2/1987 | Ales et al. .................... 2/400 |
| 4,646,362 A | 3/1987 | Heran et al. .................... 2/400 |
| 4,650,481 A | 3/1987 | O'Connor et al. ........... 604/380 |
| 4,657,539 A | 4/1987 | Hasse .................... 504/385 A |
| 4,661,102 A | 4/1987 | Shikata et al. .......... 604/385 A |
| 4,662,877 A | 5/1987 | Williams .................... 604/385 A |
| 4,663,220 A | 5/1987 | Wisneski et al. ............ 428/221 |
| 4,671,793 A | 6/1987 | Hults et al. ............. 604/385 R |
| 4,673,402 A | 6/1987 | Weisman et al. ............ 604/368 |
| 4,675,015 A | 6/1987 | Brown .................... 604/385 R |
| 4,680,030 A | 7/1987 | Coates et al. ................ 604/391 |
| 4,681,581 A | 7/1987 | Coates .................... 604/391 |
| 4,687,477 A | 8/1987 | Suzuki et al. ........... 604/385 A |
| 4,695,278 A | 9/1987 | Lawson .................... 604/385 A |
| 4,699,622 A | 10/1987 | Toussant et al. ............. 604/389 |
| 4,701,172 A | 10/1987 | Stevens .................... 604/385 A |
| 4,701,179 A | 10/1987 | Kellenberger et al. ....... 604/394 |
| 4,704,116 A | 11/1987 | Enloe .................... 604/385 A |
| 4,704,117 A | 11/1987 | Mitchell .................... 604/391 |
| 4,705,710 A | 11/1987 | Matsuda .................... 428/92 |
| 4,710,414 A | 12/1987 | Northrup et al. ............. 428/43 |
| 4,725,473 A | 2/1988 | Van Gompel et al. ....... 428/156 |
| 4,728,326 A | 3/1988 | Gilles .................... 604/391 |
| 4,738,677 A | 4/1988 | Foreman .................... 604/385 R |
| 4,743,242 A | 5/1988 | Grube et al. |
| 4,743,246 A | 5/1988 | Lawson .................... 604/385 A |
| 4,753,649 A | 6/1988 | Pazdernik .................... 604/389 |
| 4,753,650 A | 6/1988 | Williams .................... 604/389 |
| 4,753,840 A | 6/1988 | Van Gompel ................ 428/171 |
| 4,761,318 A | 8/1988 | Ott et al. .................... 428/85 |
| 4,770,656 A | 9/1988 | Proxmire et al. ................ 604/393 |
| 4,770,917 A | 9/1988 | Tochacek et al. ............. 428/95 |
| 4,772,282 A | 9/1988 | Oakley .................... 604/385.1 |
| 4,773,906 A | 9/1988 | Krushel .................... 604/391 |
| 4,776,068 A | 10/1988 | Smirlock et al. ................ 24/442 |
| 4,778,701 A | 10/1988 | Pape et al. .................... 428/40 |
| 4,794,028 A | 12/1988 | Fischer .................... 428/100 |

| | | | |
|---|---|---|---|
| 4,795,452 A | 1/1989 | Blaney et al. | 604/385.1 |
| 4,795,454 A | 1/1989 | Dragoo | 604/385.2 |
| 4,798,603 A | 1/1989 | Meyer et al. | 604/378 |
| 4,808,176 A | 2/1989 | Kielpikowski | 604/385.2 |
| 4,822,435 A | 4/1989 | Igaue et al. | 156/164 |
| 4,834,738 A | 5/1989 | Kielpikowski et al. | 604/385.2 |
| 4,834,740 A | 5/1989 | Suzuki et al. | 604/385.2 |
| 4,834,742 A | 5/1989 | Wilson et al. | 604/389 |
| 4,835,795 A | 6/1989 | Lonon | 2/408 |
| 4,846,815 A | 7/1989 | Scripps | 604/391 |
| 4,846,823 A | 7/1989 | Enloe | 604/385.2 |
| 4,847,134 A | 7/1989 | Fahrenkrug et al. | 428/138 |
| 4,850,988 A | 7/1989 | Aledo et al. | 604/385.1 |
| 4,853,070 A | 8/1989 | Erb et al. | 156/436 |
| 4,854,136 A | 8/1989 | Coslovi et al. | 66/191 |
| 4,857,067 A | 8/1989 | Wood et al. | 604/389 |
| 4,861,399 A | 8/1989 | Rajala et al. | 156/66 |
| 4,861,652 A | 8/1989 | Lippert et al. | 428/284 |
| 4,869,724 A | 9/1989 | Scripps | 604/389 |
| 4,870,725 A | 10/1989 | Dubowik | 24/442 |
| 4,880,420 A | 11/1989 | Pomparelli | 604/385.1 |
| 4,883,480 A | 11/1989 | Huffman et al. | 604/385.1 |
| 4,884,713 A | 12/1989 | Handler | 220/23.4 |
| 4,886,697 A | 12/1989 | Perdelwitz, Jr et al. | 428/192 |
| 4,887,338 A | 12/1989 | Handler | 24/306 |
| 4,887,339 A | 12/1989 | Bellanger | 24/575 |
| 4,891,868 A | 1/1990 | Watanabe | 24/691 |
| 4,892,528 A | 1/1990 | Suzuki et al. | 604/385.2 |
| 4,894,060 A * | 1/1990 | Nestegard | 604/391 |
| 4,895,568 A | 1/1990 | Enloe | 604/385.2 |
| 4,904,251 A | 2/1990 | Igaue et al. | 604/385.2 |
| 4,909,803 A | 3/1990 | Aziz et al. | 604/385.2 |
| 4,910,062 A | 3/1990 | Zinke et al. | 428/95 |
| 4,916,005 A | 4/1990 | Lippert et al. | 428/192 |
| 4,917,696 A | 4/1990 | De Jonckheere | 604/385.2 |
| 4,920,617 A | 5/1990 | Higashinaka | 24/442 |
| 4,931,343 A | 6/1990 | Becker et al. | 428/95 |
| 4,931,344 A | 6/1990 | Ogawa et al. | 428/100 |
| 4,936,840 A | 6/1990 | Proxmire | 604/385.2 |
| 4,938,753 A | 7/1990 | Van Gompel et al. | 604/385.2 |
| 4,938,754 A | 7/1990 | Mesek | 604/385.2 |
| 4,938,757 A | 7/1990 | Van Gompel et al. | 604/396 |
| 4,940,464 A | 7/1990 | Van Gompel et al. | 604/396 |
| 4,946,527 A | 8/1990 | Battrell | 156/60 |
| 4,955,113 A | 9/1990 | Rajala et al. | 24/448 |
| 4,963,140 A | 10/1990 | Robertson et al. | 604/389 |
| 4,973,326 A | 11/1990 | Wood et al. | 604/391 |
| 4,978,570 A | 12/1990 | Heyn et al. | 428/231 |
| 4,981,480 A | 1/1991 | Gaudet et al. | 604/386 |
| 4,984,339 A | 1/1991 | Provost et al. | 24/452 |
| 4,988,344 A | 1/1991 | Reising et al. | 604/368 |
| 4,988,346 A | 1/1991 | Pfefferkorn | 604/389 |
| 4,988,560 A | 1/1991 | Meyer et al. | 428/297 |
| 4,994,054 A | 2/1991 | Pigneul et al. | 604/391 |
| 4,999,067 A | 3/1991 | Erb et al. | 156/73.1 |
| 5,019,065 A | 5/1991 | Scripps | 604/385.1 |
| 5,019,066 A | 5/1991 | Freeland et al. | 604/385.2 |
| 5,019,072 A | 5/1991 | Polski | 604/389 |
| 5,019,073 A | 5/1991 | Roessler et al. | 604/391 |
| 5,032,122 A | 7/1991 | Noel et al. | 604/391 |
| 5,040,275 A | 8/1991 | Eckhardt et al. | 24/447 |
| 5,049,145 A | 9/1991 | Flug | 604/391 |
| 5,053,028 A * | 10/1991 | Zoia et al. | 604/385.21 |
| 5,058,247 A | 10/1991 | Thomas et al. | 24/448 |
| 5,077,870 A | 1/1992 | Melbye et al. | 24/452 |
| 5,100,400 A | 3/1992 | Mody et al. | 604/391 |
| 5,108,384 A | 4/1992 | Goulait | 604/390 |
| 5,135,522 A | 8/1992 | Fahrenkrug et al. | 604/385.1 |
| 5,147,347 A | 9/1992 | Huang et al. | 604/390 |
| 5,149,573 A | 9/1992 | Kobe et al. | 428/93 |
| 5,176,668 A | 1/1993 | Bernardin | 604/368 |
| 5,176,670 A * | 1/1993 | Roessler | 604/385.1 |
| 5,176,671 A | 1/1993 | Roessler et al. | 604/391 |
| 5,176,672 A | 1/1993 | Bruemmer et al. | 604/385.1 |
| 5,180,534 A | 1/1993 | Thomas et al. | 264/145 |
| 5,192,606 A | 3/1993 | Proxmire et al. | 428/284 |
| 5,196,000 A | 3/1993 | Clear et al. | 604/385.2 |
| 5,212,853 A | 5/1993 | Kaneko | 24/452 |
| 5,221,274 A | 6/1993 | Buell et al. | 604/385.2 |
| 5,221,276 A | 6/1993 | Battrell | 604/389 |
| 5,226,992 A | 7/1993 | Norman | 156/62.4 |
| 5,234,423 A | 8/1993 | Alemany et al. | 604/385.2 |
| 5,242,436 A | 9/1993 | Weil et al. | 604/385.2 |
| 5,269,776 A | 12/1993 | Lancaster et al. | 604/387 |
| 5,279,604 A | 1/1994 | Robertson et al. | 604/389 |
| 5,288,546 A * | 2/1994 | Roessler | 604/385.1 |
| 5,318,555 A * | 6/1994 | Siebers et al. | 604/390 |
| 5,358,500 A | 10/1994 | Lavon et al. | |
| 5,401,267 A * | 3/1995 | Couture-Dorschner et al. | 604/384 |
| 5,401,275 A * | 3/1995 | Flug | 604/385.1 |
| 5,509,915 A | 4/1996 | Hanson et al. | |

FOREIGN PATENT DOCUMENTS

| | | |
|---|---|---|
| DE | 88591 | 12/1921 |
| DE | 906 365 | 3/1954 |
| DE | 1 070 779 | 12/1959 |
| DE | 1 435 886 | 10/1965 |
| DE | 1 808 518 | 11/1968 |
| DE | 2 322 492 | 11/1974 |
| DE | 2 504 210 | 2/1975 |
| DE | 33 17 117 A1 | 5/1983 |
| DE | 35 33 881 A1 | 9/1985 |
| EP | 0 013 463 A1 | 7/1980 |
| EP | 0 080 647 A1 | 6/1983 |
| EP | 0 110 010 A1 | 6/1984 |
| EP | 0 131 490 A1 | 1/1985 |
| EP | 0 155 155 A2 | 9/1985 |
| EP | 0 187 725 B1 | 7/1986 |
| EP | 0 191 355 A1 | 8/1986 |
| EP | 0 194 453 A1 | 9/1986 |
| EP | 0217032 A3 | 4/1987 |
| EP | 0 233 364 A2 | 8/1987 |
| EP | 0 235 014 B1 | 9/1987 |
| EP | 0 240 213 A1 | 10/1987 |
| EP | 0 262 447 A2 | 4/1988 |
| EP | 0 276 890 A2 | 8/1988 |
| EP | 0276970 A2 | 8/1988 |
| EP | 0 278 866 A1 | 8/1988 |
| EP | 0 319 249 A1 | 6/1989 |
| EP | 0 321 232 A1 | 6/1989 |
| EP | 0 321 234 A1 | 6/1989 |
| EP | 0 324 577 A1 | 7/1989 |
| EP | 0 324 578 | 7/1989 |
| EP | 0 338 680 | 10/1989 |
| EP | 0 374 730 | 6/1990 |
| EP | 0 396 050 | 11/1990 |
| EP | 0 403 832 | 12/1990 |
| EP | 0 476 992 | 3/1992 |
| EP | 0 529 681 | 3/1993 |
| EP | 0 734 243 B1 | 6/2000 |
| FR | 0 594 375 | 9/1925 |
| FR | 2 050 837 | 4/1971 |
| FR | 2 105 683 | 4/1972 |
| FR | 2 335 165 | 7/1977 |
| FR | 2 558 691 | 8/1985 |
| FR | 2 564 298 | 11/1985 |
| FR | 2 594 650 | 8/1987 |
| FR | 2 606 257 | 5/1988 |

| | | |
|---|---|---|
| GB | 493819 | 10/1938 |
| GB | 678769 | 9/1952 |
| GB | 918084 | 2/1963 |
| GB | 1067730 | 5/1967 |
| GB | 1095397 | 12/1967 |
| GB | 1299897 | 12/1972 |
| GB | 1318957 | 5/1973 |
| GB | 1326098 | 8/1973 |
| GB | 1428572 | 3/1976 |
| GB | 1430747 | 4/1976 |
| GB | 1516287 | 7/1978 |
| GB | 1523018 | 8/1978 |
| GB | 2035053 A | 6/1980 |
| GB | 2074011 A | 10/1981 |
| GB | 2091986 A | 8/1982 |
| GB | 2101875 A | 1/1983 |
| GB | 2129689 B | 5/1984 |
| GB | 2131346 B | 6/1984 |
| GB | 2135568 A | 9/1984 |
| GB | 2142241 A | 1/1985 |
| GB | 2142242 A | 1/1985 |
| GB | 2142541 A | 1/1985 |
| GB | 2142542 A | 1/1985 |
| GB | 2144637 A | 3/1985 |
| GB | 2148095 A | 5/1985 |
| GB | 2 162 737 A | 2/1986 |
| GB | 2164542 A | 3/1986 |
| GB | 2165457 A | 4/1986 |
| GB | 2185383 A | 7/1987 |
| GB | 2209672 A | 5/1989 |
| GB | 2233876 A | 1/1991 |
| GB | 2 284 742 A | 6/1995 |
| JP | 49-25293 | 3/1974 |
| JP | 49-25294 | 3/1974 |
| JP | 49-25395 | 3/1974 |
| JP | 49-48798 | 4/1974 |
| JP | 49-48999 | 4/1974 |
| JP | 49-79097 | 7/1974 |
| JP | 49-88599 | 8/1974 |
| JP | 49-115139 | 10/1974 |
| JP | 49-120438 | 10/1974 |
| JP | 49-129391 | 11/1974 |
| JP | 49-137728 | 11/1974 |
| JP | 49-144438 | 12/1974 |
| JP | 50-87791 | 7/1975 |
| JP | 53-158440 | 12/1978 |
| JP | 54-105738 U | 7/1979 |
| JP | 56-11243 A | 2/1981 |
| JP | 56-42909 U | 4/1981 |
| JP | 57-138908 U | 8/1982 |
| JP | 57-161101 A | 10/1982 |
| JP | 57-191303 A | 11/1982 |
| JP | 57-191304 A | 11/1982 |
| JP | 58-143809 | 9/1983 |
| JP | 59-165407 U | 11/1984 |
| JP | 60-9908 U | 1/1985 |
| JP | 63-2708 U | 1/1988 |
| JP | 63-131710 | 8/1988 |
| JP | 63-61402 | 11/1988 |
| JP | 1-168901 A | 7/1989 |
| JP | 56-70812 U | 10/1995 |
| JP | 55-103208 | 10/1995 |
| JP | 59-88407 U | 11/1995 |
| WO | WO 83/03754 | 11/1983 |
| WO | WO 84/04242 | 11/1984 |
| WO | WO 86/02263 | 4/1986 |
| WO | WO 94/26220 A1 | 11/1994 |
| WO | WO 95/05140 | 2/1995 |
| WO | WO 95/25496 | 9/1995 |

OTHER PUBLICATIONS

Further submission dated Oct. 11, 2001, from Counselor Hayes for SCA Hygiene Products AB with enclosures including letter from 3M Laboratories dated Sep. 5, 2001, with its enclosure in the Opposition to European Patent 0 800 379 B1.

Patentee's observations dated May 24, 2001, in response to Notices of Opposition (Opposition to European Patent 0 800 379 B1).

Communication of a Notice of Opposition enclosing Notice of Opposition by Koester GmbH & Co. KG dated Aug. 28, 2000, to European Patent 0 800 379 B1.

Communication of a Notice of Opposition enclosing Notice of Opposition by 3M Innovative Properties Co. dated Aug. 28, 2000, to European Patent 0 800 379 B1.

Communication of a Notice of Opposition enclosing Notice of Opposition by SCA Hygiene Products AB dated Aug. 28, 2000, including Statement of Facts and Submissions to European Patent 0 800 379 B1.

Abandoned U.S. Appl. No. 07/007,841, entitled "Disposable Diaper Having An Improved Fastening Device" filed Jan. 26, 1987 in the name of Charles L. Scripps.

Abandoned U.S. Appl. No. 07/040,520, entitled "Loop Fastening Material For Fastening Device And Method Of Making Same" filed Apr. 24, 1987 in the name of John R. Noel et al.

Abandoned U.S. Appl. No. 07/078,345, entitled "Disposable Diaper Having Wide Tapered Fastening Tapes" filed Jul. 28, 1987 in the name of Harold R. Burkhard et al.

UPDATE 84 "Absorbent Products Markets Part 1, (Tampons, Diapers, Feminine Pads)," vol. 1, Diapers; published by Marketing/Technology Service, Dec. 1984, Section III, pp. 27–28.

"And Vencro Fitted Nappies," *Medical Textiles*, vol. 1, No. 1, May 1984, pp. 11–12.

"Easy–To–Fit Reusable Diaper," *Medical Textiles*, vol. 3, No. 1, May 1986, pp. 9–10.

"A Gripping Success," *Dupont Magazine*, May/Jun. 1985, pp. 26–27.

Lambert, Brian, "Hook & Loop Fasteners," *Industrial Fabric Products Review*, Sep. 1985, pp. 45–47.

Wilson, Timothy, "Closures Become Fashion," *Bobbin Magazine*, Dec. 1986, pp. 94–98.

Fraser, Dr. Annette J., "Closing In On New Markets," *Bobbin Magazine*, Dec. 1987, pp. 104–109.

"AMF Hook & Loop Tape Attacher Programmed For Industrial Uses," *Bobbin Magazine*, Apr. 1987, p. 130.

"Your Baby's First Year" (Time–Life Book Inc. 1986), pp. 38–41.

"Consumer Guide® Baby Equipment Buying Guide" Signet (Copyright Publications International, Ltd., 1985), pp. 106–109.

"Poly–Lock Fastener Has Industrial Applications," *Industrial Fabrics Products Review*, Nov. 1986, pp. 62, 64.

Instruction panel for PAMPERS® Phases diapers, with Warning, Caution, disposal information, Packaging Information, and Product Information, P&G, 1990.

Communication—European Search Report—EP 91 12 1581, Apr. 21, 1992.

Gershman, M.D., Maurice, "Self–Adhering Nylon Tapes," *Journal of the American Medical Association*, vol. 168, No. 7, Oct. 18, 1958.

Information set forth in paragraph A on p. 3 of this Information Disclosure Statement.

Information set forth in paragraph B on p. 3 of this Information Disclosure Statement.
Information set forth in paragraph C on p. 3 of this Information Disclosure Statement.
Information set forth in paragraph D on p. 3 of this Information Disclosure Statement.
TAPPI Method T543 om–94 "Bending Resistance of Paper" (Gurley Type Tester); provisional method—1984, official method—1994, pp. 1–5.
Communication dated Apr. 3, 2003, to the European Patent Office from Frank B. Dehn & Co. 23 pages.
Communication dated Oct. 17, 2003, to the European Patent Office from Boult Wade Tennant, 6 pages.
Communication dated Nov. 17, 2003, to the European Patent Office from Frank B. Dehn & Co., 2 pages.
Communication dated Nov. 19, 2003, to the European Patent Office from Vossius & Partner, 7 pages.
Communication dated Mar. 12, 2004, to the European Patent Office from Boult Wade Tennant, 3 pages.
Communication dated May 19, 2004, to the European Patent Office from Frank B. Dehn & Co., 6 pages.
Communication dated Jul. 6, 2004, to the European Patent Office from Boult Wade Tennant, 1 page.
Communication of the Technical Board of Appeal 3.2.6 dated Sep. 9, 2004, 7 pages.
Communication dated Mar. 7, 2005, to the European Patent Office from Frank B. Dehn & Co., 26 pages.
Communication dated Mar. 7, 2005, to the European Patent Office from Vossius & Partner, 8 pages.
Communication dated Apr. 4, 2005, to the European Patent Office from Boult Wade Tennant, 4 pages.
Minutes of the public oral proceedings before the Technical Board of Appeal held Apr. 7, 2005, 3 pages.
Notice of withdrawal of appeal in opposition to EP 0800379 dated Apr. 13, 2005, 1 page.

* cited by examiner

FLEXIBLE MECHANICAL FASTENING TAB

BACKGROUND OF THE INVENTION

The present invention relates to a mechanical fastening tab suitable for use on a disposable absorbent product. Specifically, the present invention relates to a mechanical fastening tab having improved flexibility.

Disposable absorbent products such as diapers, adult incontinence products, and the like are known to those skilled in the art. Similarly, mechanical fastening means for fastening such absorbent products about the waist of a wearer are similarly known to those skilled in the art. Examples of known mechanical fasteners include hook-and-loop type fasteners.

Unfortunately, mechanical fasteners such as hook-and-loop type fasteners have not been widely used on commercial disposable absorbent products. One reason for the fact that mechanical fasteners have not been widely used commercially on disposable absorbent products is that such mechanical fasteners tend to be relatively expensive and thus difficult to use economically on a disposable product. This is particularly true when the mechanical fasteners are designed to have fastening properties which render them suitable for use on disposable absorbent products. Similarly, mechanical fasteners which are inexpensive enough to use on a disposable absorbent product tend to have fastening properties which are insufficient for satisfactory use on disposable absorbent products.

Specifically, in use, mechanical fasteners on disposable absorbent products are generally subjected to both shear and peel forces. As used herein, shear forces are intended to refer to forces which are applied to the mechanical fasteners in a plane generally parallel to the plane of attachment between the fastener components. Peel forces are intended to refer to a force applied at an angle of 90 degrees or greater to separate the fastener components of a mechanical fastening tab in a peeling fashion. A mechanical fastener which does not possess sufficient resistance to shear and peel forces would, in use on a disposable absorbent product, tend to disengage, resulting in the disposable absorbent product losing its securement about the waist of a wearer. This is, obviously, undesirable.

Accordingly, it is desirable to provide mechanical fasteners suitable for use on disposable absorbent products, which mechanical fasteners are inexpensive enough to render their use on a disposable product feasible, and yet which possess sufficient resistance to peel and shear forces to produce a disposable absorbent product which is satisfactory in use. It is to this goal that the present invention is directed.

SUMMARY OF THE INVENTION

The present invention relates to a mechanical fastening tab for use on a disposable absorbent product. The fastening tab comprises a substrate adapted to be joined to said disposable absorbent product. The fastening tab further comprises a first mechanical fastener component joined to said substrate. The first mechanical fastener component is adapted to releasably engage with a second mechanical fastener component. The fastening tab has a Gurley stiffness value of less than about 1000 milligrams in an area of said fastening tab including said first mechanical fastener component.

In a second aspect, the present invention relates to a disposable product comprising an outer cover, and, optionally, a bodyside liner, and an absorbent core located between said outer cover and said bodyside liner. The disposable product further comprises a mechanical fastening tab, said mechanical fastening tab comprising a substrate joined to said disposable absorbent product and a first mechanical fastener component joined to said substrate. The first mechanical fastener component is adapted to releasably engage with said outer cover. The fastening tab has a Gurley stiffness value of less than about 1000 milligrams in an area of said fastening tab including said first mechanical fastener component.

In another aspect, the present invention relates to a disposable absorbent product comprising an outer cover, a bodyside liner and an absorbent core located between the outer cover and the bodyside liner. The outer cover comprises a film material having attached thereto a nonwoven material to form a laminate. The laminate has a Gurley stiffness value of less than 100 milligrams. The disposable absorbent product further comprises a mechanical fastening tab. The mechanical fastening tab comprises a substrate joined to the disposable absorbent product and a first mechanical fastener component joined to the substrate. The first mechanical fastener component is adapted to releasably engage with the laminate. The fastening tab has a Gurley stiffness value of less than about 1000 milligrams in an area of the fastening tab including the first mechanical fastener. In one specific embodiment, when the first mechanical fastener component is releasably engaged with the laminate and is subjected to shear forces, the laminate deforms to dissipate a portion of said shear forces.

In another aspect, the present invention relates to a disposable product comprising an outer cover having attached thereto a second mechanical fastener component. The product further includes a mechanical fastening tab. The mechanical fastening tab comprises a substrate joined to said disposable product and a first mechanical fastener component joined to said substrate. The first mechanical fastener component is adapted to releasably engage with the second mechanical fastener component. The fastening tab has a Gurley stiffness value of less than about 1000 milligrams in an area of said fastening tab including said first mechanical fastener component.

DETAILED DESCRIPTION OF THE INVENTION

Figure 1:
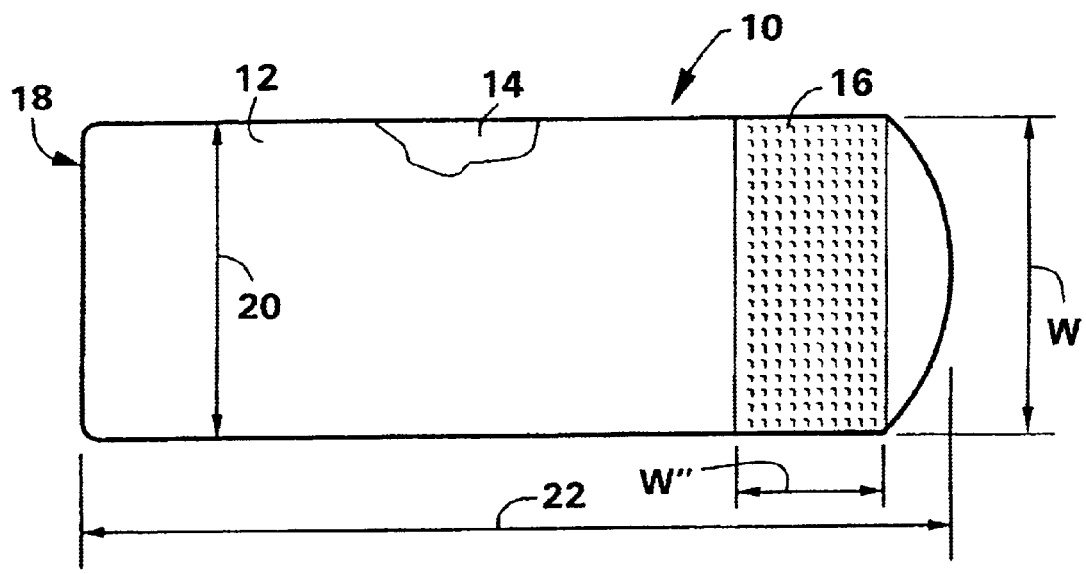
FIG. 1 illustrates one embodiment of a fastening tab according to the present invention.

The present invention relates to a mechanical fastening tab suitable for use on a disposable absorbent product. The present invention can best be understood by reference to the drawings wherein FIG. 1 illustrates a fastening tab according to the present invention. Fastening tab 10 comprises a first substrate 12 and a second substrate 14 joined to the first substrate 12. The first substrate 12 and/or the second substrate 14 are adapted to be joined to a disposable absorbent product.

A first mechanical fastener component 16 is joined to the first substrate 12. The first mechanical fastener component is adapted to releasably engage with a second mechanical fastener component. The fastening tab 10 has a Gurley stiffness value of less than about 1000 milligrams in an area of said fastening tab including said mechanical fastener component 16.

Transverse end 18 of fastening tab 10 is adapted to be attached to a disposable absorbent product to form a manufacturer's bond end of the fastening tab 10. The manufacturer's bond end refers to the portion of the fastening tab 10 which includes a bond which attaches the fastening tab to the disposable absorbent product, which bond is formed during the manufacturing process of the disposable absorbent product. The bond which defines the manufacturer's bond end is generally intended to be a permanent bond which can only be destructively broken to remove the fastening tab from the disposable absorbent product.

The disposable absorbent product to which the fastening tab 10 is attached will have a machine direction (MD) and a cross-machine direction (CD). The machine direction is intended to refer to that direction which corresponds to the length (as defined by the longitudinal centerline) of the product. The cross-machine direction refers to a direction generally perpendicular to the machine direction. The dimension of the fastening tab 10 which is generally parallel to the machine direction of the product to which fastening tab 10 is attached will similarly be considered the machine direction of fastening tab 10. That is, the machine direction of the fastening tab 10 will be that direction generally parallel to the machine direction of the product to which fastening tab 10 is intended to be joined. In the illustrated embodiment, the direction indicated by arrow 20 indicates the machine direction of the fastening tab 10. The direction indicated by arrow 22 generally corresponds to the cross-machine direction of the fastening tab 10 in that it is generally parallel to the cross-machine direction of the disposable absorbent product to which fastening tab 10 is intended to be joined (see FIG. 1).

Figure 2:
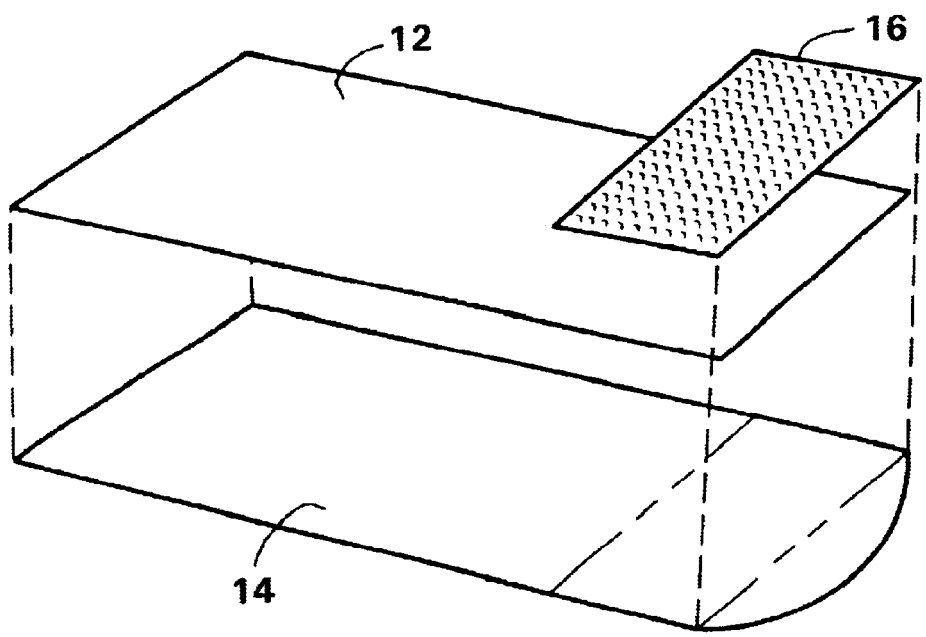
FIG. 2 illustrates an exploded perspective view of the fastening tab illustrated in FIG. 1.

FIG. 2 illustrates an exploded perspective view of the fastening tab 10 illustrated in FIG. 1. While the fastening tab illustrated in FIG. 1 and FIG. 2 are shown as comprising a first and second substrate, it is to be understood that the fastening tab illustrated in FIGS. 1 and 2 could similarly be formed from a single substrate corresponding to either the first or second substrate.

As used herein, reference to a first mechanical fastener component is intended to refer to a material which is adapted to mechanically interlock with a second material. Any such material is suitable for use as the first mechanical fastener component. In the illustrated embodiment, the first mechanical fastener component is the hook portion of a hook-and-loop fastener. Hook-and-loop fasteners are known to those skilled in the art. A hook-and-loop fastener generally comprises a hook material and a loop material. The hook material generally comprises a base sheet material from which stemlike projections extend. One end of the stemlike projection is attached to the base sheet material, while the other end of the stemlike projection defines a hook, or hook-like structure such as a mushroom, which is adapted to interlock with a loop or loop-like material. The loop or loop-like material generally comprises a knit, woven or nonwoven material defining individual loops of material which can interlock with the hook-like material. The loop or loop-like material may be attached to a substrate to form a laminate.

Exemplary of a hook material suitable for use in the present invention is that obtained from Velcro Group Company, Manchester, N.H., under the trade designation CFM-22-1097; CFM-22-1121; CFM-22-1162; CFM-25-1003; CFM-29-1003. Suitable hook materials generally comprise from about 100 to about 4000 hooks per square inch (about 16 to about 620 hooks per square centimeter), alternatively from about 800 to about 2500 hooks per square inch (about 124 to about 388 hooks per square centimeter), alternatively from about 1000 to about 2000 hooks per square inch (about 155 to about 310 hooks per square centimeter). The hooks suitably have a height of from about 0.001 inch (0.00254 centimeter) to about 0.075 inch (0.19 centimeter), alternatively of from about 0.015 inch (0.0381 centimeter) to about 0.03 inch (0.0762 centimeter).

Other hook materials suitable for use in the present invention include a hook material available from the Minnesota Mining and Manufacturing Company, St. Paul, Minn., under the designation CS 200.

The hook material of the present invention may be formed from a polymeric material having a flexural modulus greater than about 30 kilopounds per square inch (kpsi), suitably of from about 50 kpsi to about 300 kpsi, alternatively of from about 150 kpsi to about 50 kpsi.

When the polymeric material from which the hook material of the present invention is formed has a relatively high flexural modulus, this property tends to render the hook material less flexible. This, in turn, tends to cause the fastening tab to have a relatively high Gurley stiffness value. Accordingly, when the polymeric material from which the hook material is formed has a relatively high flexural modulus, it is desirable to alter other aspects of the fastening tab or hook material to meet the Gurley stiffness targets described above.

For example, the base sheet material from which the stemlike hook projections extend can be fabricated to be much thinner than normally associated with known hook materials. For example, the base sheet material from which the hooks extend may have a thickness of from about 0.001 inch to about 0.020 inch (about 0.00254 centimeter to about 0.0508 centimeter), alternatively of from about 0.002 inch to about 0.015 inch (about 0.00508 centimeter to about 0.0381 centimeter).

The use of a polymeric material having a relatively high flexural modulus has generally been found to increase the peel strength of a hook material when engaged with a loop material. Accordingly, in one embodiment, a polymeric material from which the hook material is formed has a flexural modulus of greater than about 100 kpsi.

In an alternative embodiment, the polymeric material from which the hook material is formed is relatively soft and has a flexural modulus less than about 50 kpsi. Due to the soft nature of such polymeric materials, it is generally possible to employ a hook material having a thicker base sheet and still produce a fastening tab having a desirable Gurley stiffness value.

Other aspects of hook material design can affect the flexibility of the hook material. For example, hook orientation, spacing, backing thickness, hook thickness, and the like. Such aspects of hook design affect the flexibility of the hook material in both the machine and cross machine directions.

Any flexible material having the required physical strength to perform a fastening function as described herein is believed suitable for use as the first and/or second substrate material. Examples of materials suitable for use as the first and second substrate material include thermoplastic or thermosetting films such as polyolefin films, polyurethane films, and the like; nonwoven materials such as meltblown or spunbond polyolefin; woven materials; nonwoven composites; nonwoven/film composites; and the like. Elastomerically stretchable webs can also be used as the first and/or second substrate material. The elastomeric webs can be composed of a stretch-bonded-laminate (SBL) material, a neck-bonded-laminate (NBL) material, an elastomeric film, an elastomeric foam material, or the like. For example, suitable meltblown elastomeric fibrous webs are described in U.S. Pat. No. 4,663,220 issued May 5, 1987, to A. Wisneski et al., the disclosure of which is hereby incorporated by reference. Examples of composite fabrics comprising at least one layer of nonwoven textile fabric secured to a fibrous elastic layer are described in European Patent Application No. EP 0 110 010 published on Apr. 8, 1987, with the inventors listed as J. Taylor et al., the disclosure of which is hereby incorporated by reference. Examples of NBL materials are described in U.S. Pat. No. 5,226,992 issued Jul. 13, 1993, to Mormon, the disclosure of which is hereby incorporated by reference. When the substrate comprises a thermoplastic or thermosetting film, the substrate may be integrally formed with the first mechanical fastener component. That is, the substrate may comprise an extension of the backing of the first mechanical fastener component.

Naturally, the physical properties of the first and/or second substrate materials will affect the flexibility of the fastening tab illustrated in FIG. 1. Accordingly, it is generally desired that the first and/or second substrate materials be selected to be relatively flexible, thus enabling the fastening tab of the present invention to possess the desired Gurley stiffness value. Specifically, it is desired that the first and/or second substrate materials have a Gurley stiffness value of less than about 1000 milligrams, alternatively of less than about 200 milligrams, alternatively of less than about 75 milligrams measured in at least the machine direction.

Any method capable of attaching the first and second substrates to one another and/or the first mechanical fastener component to the first substrate is believed suitable for use in the present invention. For example, the materials may be attached together by adhesives, thermal bonding (including ultrasonic bonding), sewing, combinations of these methods, and the like. In one preferred embodiment of the present invention, the first mechanical fastener component is attached to the first substrate with both adhesive and thermal bonds. Again, the method of attaching the first and/or second substrates together as well as the method for attaching the first mechanical fastener component to the first substrate can affect the flexibility (as measured by the Gurley stiffness) of the fastening tab. Accordingly, the method of attachment must be carefully chosen to enable the fastening tab to possess the desired Gurley stiffness value.

The fastening tabs of the present invention have a Gurley stiffness value of less than about 1000 milligrams, alternatively of less than about 500 milligrams, alternatively of less than about 200 milligrams, alternatively of less than about 75 milligrams, in an area of said fastening tab including said first mechanical fastener component. The area of said fastening tab including said first mechanical fastening component and having the Gurley stiffness values described above, is suitably at least about 1 square centimeter in size, alternatively of at least about 2 square centimeters in size.

The fastening tabs of the present invention will be considered to have the desired Gurley stiffness values when the fastening tabs have a desired Gurley stiffness value measured in either the machine or cross direction of the fastening tabs 10. It is generally desired that the fastening tabs have the desired Gurley stiffness values in both the machine and cross direction of the fastening tabs.

Figure 3:
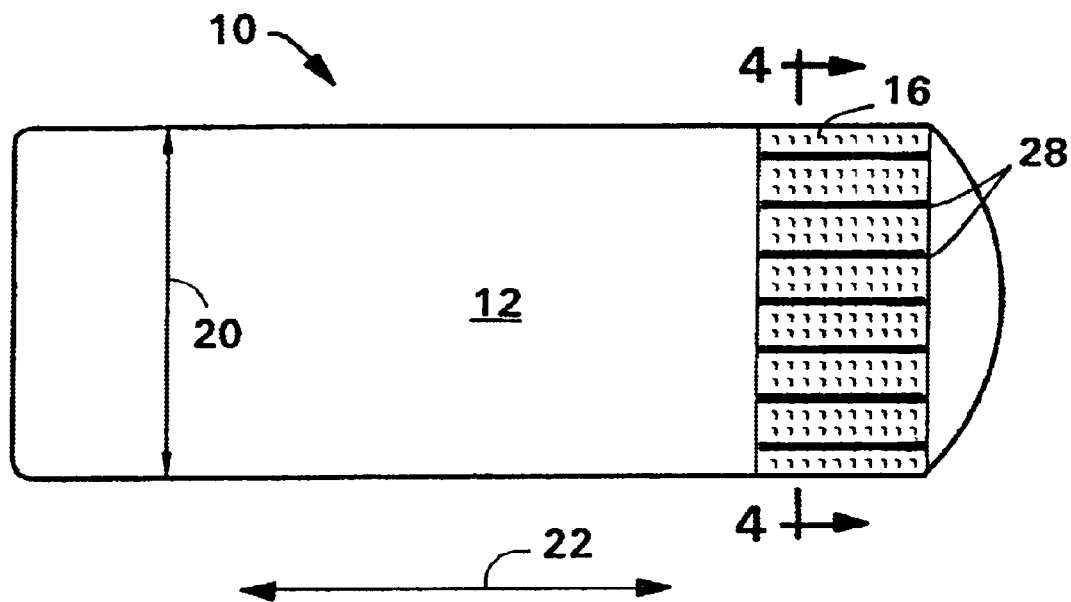
FIG. 3 illustrates one embodiment of a fastening tab according to the present invention.
Figure 4:
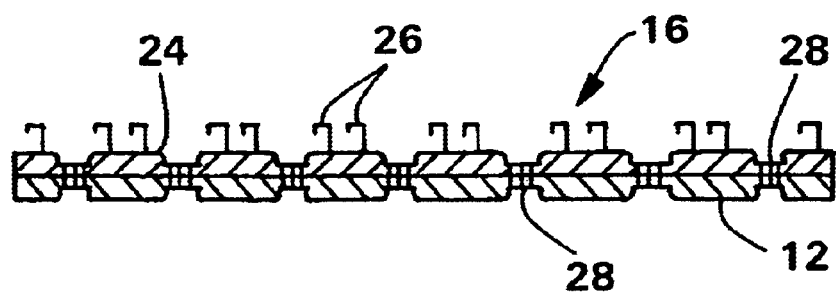
FIG. 4 is a cross-sectional view of the fastening tab illustrated in FIG. 3 taken along line 4—4 of FIG. 3.

With reference to FIGS. 3 and 4 in which like numerals represent like elements, the fastening tab 10 comprises a first substrate 12 and a first mechanical fastener component 16. As can be seen from reference to FIG. 4, the first mechanical fastener component 16 comprises a base sheet material 24 and hooks 26. The base sheet material is relatively thick and thus would tend to increase the Gurley stiffness of the fastening tab 10 illustrated in FIGS. 3 and 4. Nonetheless, the first fastening component 16 is attached to the first substrate 12 by ultrasonic bonding along bond lines 28. The presence of bond lines 28 have been found to render the fastening tab 10 illustrated in FIGS. 3 and 4 relatively flexible in the machine direction 20 of the fastening tab 10.

The bond lines 28 suitably have a width of about 0.004 inch to about 0.02 inch, alternatively from about 0.006 inch to about 0.012 inch. Similarly, the flexibility of the fastening tab 10 is affected by the frequency of the bond lines 28. Accordingly, the first mechanical fastener component 16 is suitably attached to the first substrate 12 by bond lines 28 having a frequency of about 3 to about 12 bond lines per inch, alternatively of from about 5 to about 10 bond lines per inch in the machine direction 20 of the fastening tab 10.

The fastening tabs illustrated in FIGS. 3 and 4 will, due to the presence of bond lines 28, generally be more flexible in the machine direction 20 than in the cross direction 22 of the fastening tab 10. Indeed, the presence of bond lines 28 may increase the stiffness of the fastening tab 10 in the cross direction 22 of the fastening tab. Nonetheless, as described above, as long as the fastening tab 10 has a Gurley stiffness value of less than about 1000 milligrams, improved fastening is generally achieved.

Figure 5:
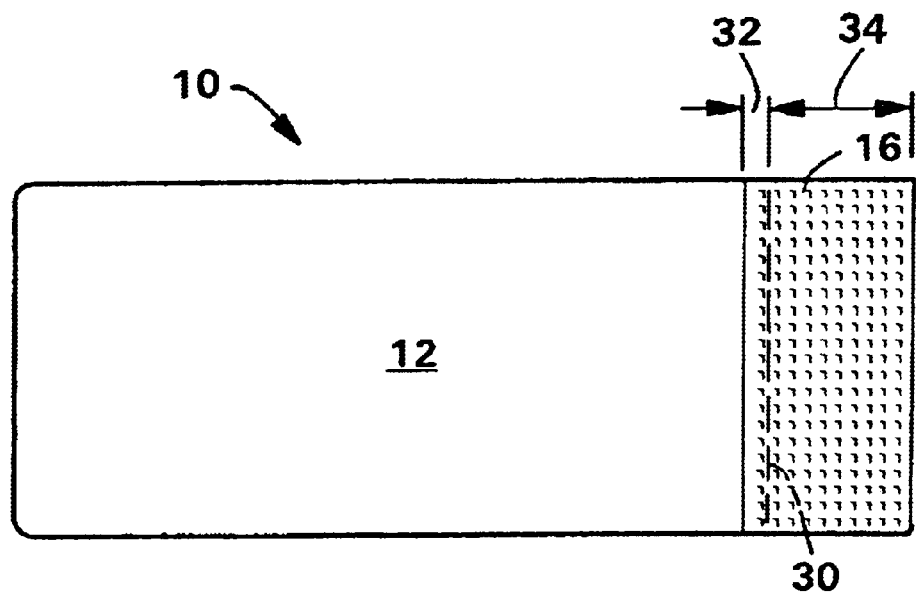
FIG. 5 is a top plan view of one embodiment of a fastening tab according to the present invention.
Figure 6:
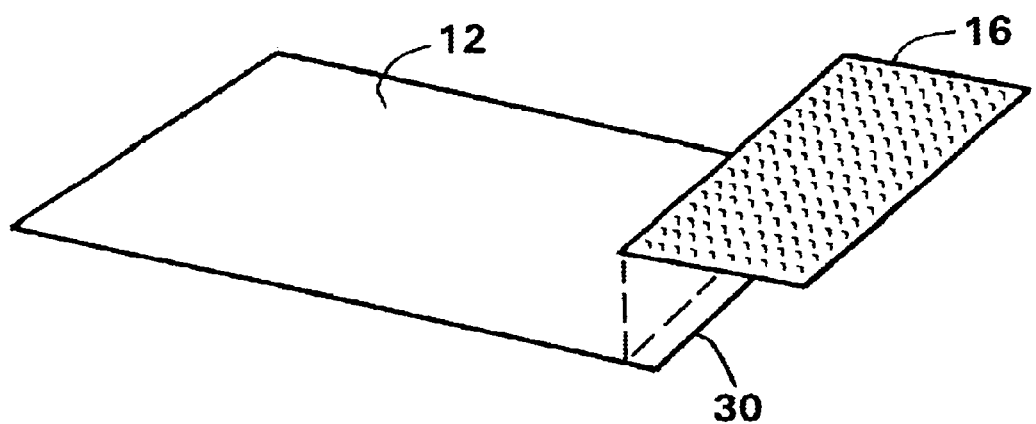
FIG. 6 is an exploded perspective view of the fastening tab illustrated in FIG. 5.

FIGS. 5 and 6 illustrate an alternative embodiment of the fastening tab according to the present invention. In the embodiment illustrated in FIGS. 5 and 6, fastening tab 10, again comprises a first substrate 12 and a first mechanical fastener component 16. As can be seen from reference to FIG. 6, the first mechanical fastener component 16 is attached to the first substrate 12 along transverse end 30 of the first substrate 12 such that the first substrate 12 incompletely overlays the first mechanical fastener component 16. That is, the first mechanical fastener component is attached to the first substrate 12 only in overlapped portion 32 and is not overlaid by the first substrate 12 in non-overlapped portion 34. By forming the fastening tab 10 such that the first mechanical fastener component 16 is not completely overlaid by the first substrate 12, the flexibility of mechanical fastening tab 10 in an area comprising the first mechanical fastener component can be improved. When the first mechanical fastener component is not completely overlaid by the first substrate, it is generally desired that from about 98 to about 2 percent, alternatively from about 98 to about 30 percent of one planar surface of the first mechanical fastener component not be overlaid by the first substrate.

In contrast, FIGS. 1–4 illustrate fastening tabs in which the first mechanical fastener component 16 is completely overlaid by the first substrate 12. That is, 100 percent of one planar surface of the first mechanical fastener component 16 is overlaid by one planar surface of the first substrate 12.

Figure 7:
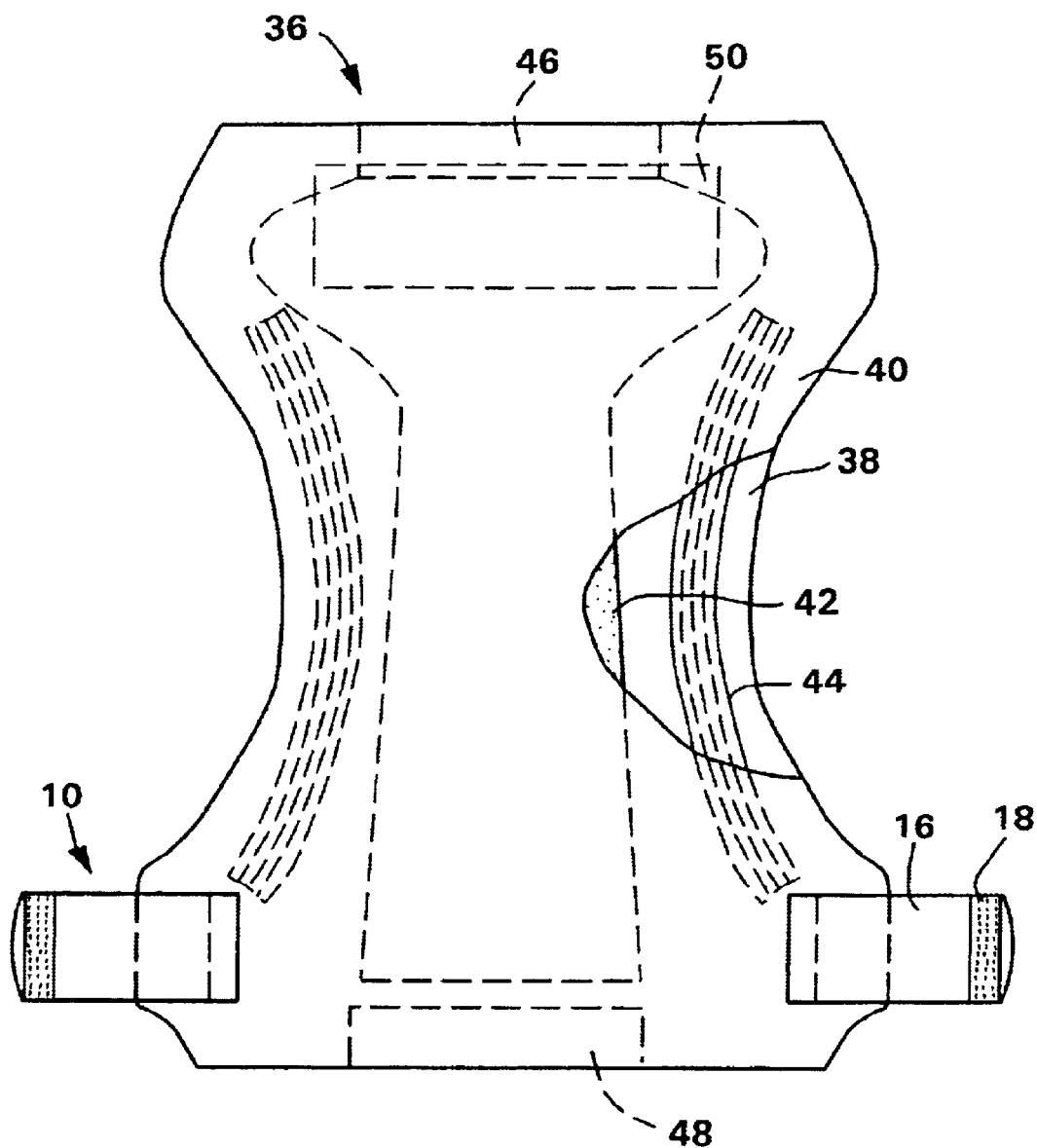
FIG. 7 is a top plan view of an infant diaper according to the present invention.
Figure 8:
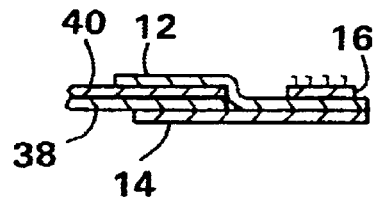
FIG. 8 is a cross-sectional view taken along line 8—8 of FIG. 7.

FIGS. 7 and 8 illustrate a fastening tab according to the present invention in use on a disposable infant diaper. While the fastening tabs of the present invention are illustrated in use on an infant diaper, it is to be understood that the fastening tabs are equally well suited for use on disposable products such as adult incontinence products and the like.

Those skilled in the art will recognize that diaper 36 generally comprises an outer cover 38, an inner bodyside liner 40, and an absorbent core 42 located between the outer cover 38 and the bodyside liner 40. Leg elastics 44 are located generally at the longitudinal edges of the diaper 36. The diaper further comprises a front waist elastic 46 and a rear waist elastic 48. The fastening tabs of the present invention are generally attached at the rear of the diaper. In the illustrated embodiment, the fastening tab illustrated has the construction illustrated in FIGS. 1 and 2. Accordingly, the fastening tab is attached by sandwiching the outer cover 38 and bodyside liner 40 between the first substrate 12 and the second substrate 14 in an area where the first and second substrates are not attached to one another. This aspect of the invention can best be seen by reference to FIG. 8. In the embodiment illustrated in FIG. 8, diaper 36 further comprises a second mechanical fastener component 50. The second mechanical fastener component is generally located at the front of the diaper 36. In the illustrated embodiment, the first mechanical fastener component comprises the hook material and the second mechanical fastener component comprises a loop material. The first and second mechanical fastener components can interlock with one another to fasten the diaper 36 about the waist of a wearer. Those skilled in the art will recognize that the relative positions of the hook-and-loop materials could be reversed on diaper 36.

Specific examples of disposable absorbent products on which the fastening tabs of the present invention may be utilized are disclosed in the following U.S. patents and patent applications: U.S. Pat. No. 4,798,603 issued Jan. 17, 1989, to Meyer et al.; U.S. Pat. No. 5,176,668 issued Jan. 5, 1993, to Bernardin; U.S. Pat. No. 5,176,672 issued Jan. 5, 1993, to Bruemmer et al.; U.S. Pat. No. 5,192,606 issued Mar. 9, 1993, to Proxmire et al.; U.S. patent application Ser. No. 08/096,654 filed Jul. 22, 1993, in the name of Hanson et al. and U.S. patent application Ser. No. 08/263,281 filed Jun. 21, 1994, in the name of Dilnik et al.

Exemplary of a loop material suitable for use as the second mechanical fastener component 50 illustrated in FIG. 7 is that obtained from Guilford Mills, Inc., Greensboro, N.C., under the trade designations Style 19902, Style 34285 or Style 30020. Other suitable loop materials are shown, for example, in U.S. Pat. No. 5,019,073 issued May 28, 1991, to Roessler et al., the disclosure of which is incorporated by reference herein. Suitable loop materials may include woven, knitted, or nonwoven materials. Suitable nonwoven materials are those formed through a spunbond or melt-blown process and have a basis weight of from about 0.1 ounce per square yard to about 2.0 ounces per square yard, alternatively of from about 0.5 ounce per square yard to about 1.25 ounce per square yard, alternatively of from about 0.75 to about 1.0 ounce per square yard. The fibers of such nonwoven material are suitably formed from polymeric materials such as polyolefins, polyamides, polyesters, rayon, combinations of the above, and the like. Such nonwoven materials generally have a fiber denier within the range of from about 1d to about 15d, preferably of from about 2d to about 5d.

The second mechanical fastener component can be a discrete element located on the outer surface of a disposable absorbent product in a manner such as that illustrated in FIG. 7. Alternatively, the second mechanical fastener component may comprise the entire outer surface of the disposable absorbent product such as when the outer cover is the second mechanical fastener component. In one specific embodiment, the outer cover of the disposable absorbent product is a film/nonwoven laminate known as a stretch thermal laminate comprising a 0.6 mil (0.015 millimeter) polypropylene blown film and 0.7 ounce per square yard (23.6 grams per square meter) polypropylene spunbond material. The spunbond material is composed of about 2.0 denier fibers. The stretch thermal laminate is formed by stretching the polypropylene film, in one direction, until it is extended by 25 percent. The spunbond polypropylene is then brought into face-to-face contact with the stretched polypropylene film. The polypropylene film and spunbond material are then thermally bonded together at spaced intervals. The resulting laminate has a plurality of separate and distinct bond sites with an overall bond area of about 13 percent per unit area. After the film and spunbond material are laminated to one another, the laminate is allowed to relax. The film layer retracts about 10 percent, thereby leaving the film permanently deformed to a length of about 15 percent greater than its original length. The process for forming the stretch thermal laminate is described in greater detail in commonly-owned copending U.S. patent application Ser. No. 07/997,800, filed Dec. 29, 1992, in the name of McCormack at al., the contents of which are incorporated herein.

Applicants have found that, when the second mechanical fastener component comprises a nonwoven material, it is generally desired that the hooks be relatively small, having a height of no more than about 0.02 inch, and being present at a density of from about 900 to about 2500 hooks per square inch (140 to about 280 hooks per square centimeter). Suitable hook materials are those described above as the CFM-25-1003, CFM-29-1003 and CS 200 hook materials.

Applicants have discovered that it is desirable to have the second mechanical fastener component be extremely flexible. Thus, the woven or knit materials such as those described above have been found to be particularly well suited for use in the present invention. For example, the loop material obtained from Guilford Mills has a Gurley stiffness value of less than about 6 milligrams. When the Guilford Mills loop material is adhesively attached to a stretch thermal laminate (STL) outer cover, the loop/STL composite has a Gurley stiffness value of less than about 40 milligrams in both the MD and CD directions. The stretch thermal laminate material described above has been found to have a Gurley stiffness value of less than about 10 milligrams in both the MD and CD directions. The stretch thermal laminate is capable of performing both the function of a liquid impervious film and a second mechanical fastener component (loop material). Thus, the Gurley stiffness of the stretch thermal laminate can represent the stiffness of the second mechanical fastener component. In contrast, the Guilford Mills loop material is attached to a substrate such as the STL material such that the loop/STL composite may represent the stiffness of the second mechanical fastener component and the material to which it is directly attached.

Applicants have discovered that it is desirable that the second mechanical fastener component itself (no other attached components) have a Gurley stiffness value of less than about 100 milligrams, alternatively of less than about 75 milligrams, alternatively of less than about 50 milligrams, alternatively of less than about 20 milligrams. It is also desired that the second mechanical fastener component and any other components of a disposable absorbent product to which it is directly attached have a Gurley stiffness value of less than about 1000 milligrams, alternatively of less than about 500 milligrams, alternatively of less than about 200 milligrams, alternatively of less than about 75 milligrams, alternatively of less than about 50 milligrams.

In one preferred embodiment of the present application, the ratio of the Gurley stiffness value of the fastening tab and the Gurley stiffness value of the second mechanical fastener component itself, is from about 1:10 to 10:1, alternatively from about 1:5 to 5:1. By having the Gurley stiffness ratio of the fastening tab and second mechanical fastening component itself be within the ranges described above, improved fastening can be achieved. In another embodiment of the present invention, the ratio of the Gurley stiffness value of the fastening tab and the Gurley stiffness value of the second mechanical fastener component and any other components of a disposable absorbent product to which the second mechanical fastener component is directly attached is from about 1:10 to 10:1, alternatively from about 1:5 to 5:1.

Further, when the fastening tab and the second mechanical fastener component itself are in an engaged relationship to form a fastener composite, it is desired that the fastener composite have a Gurley stiffness value of less than about 1000 milligrams, alternatively of less than about 500 milligrams, alternatively of less than about 200 milligrams, alternatively of less than about 75 milligrams.

In one embodiment of the present invention, the second mechanical fastener component and/or a component to which it is attached is able to deform during the application of shear forces when the fastening tab and second mechanical fastener component are engaged. For example, the second mechanical fastener component may be formed from or attached to an elastomeric material or a stretchable material having a low modulus. The ability of the second mechanical fastener component to deform when subjected to shear forces allows the shear forces being applied to the second mechanical fastener component to be dissipated over a larger area. Thus, the shear forces which are being applied are not concentrated in the area where the fastening tab is engaged with the second mechanical fastener component.

Figure 9:
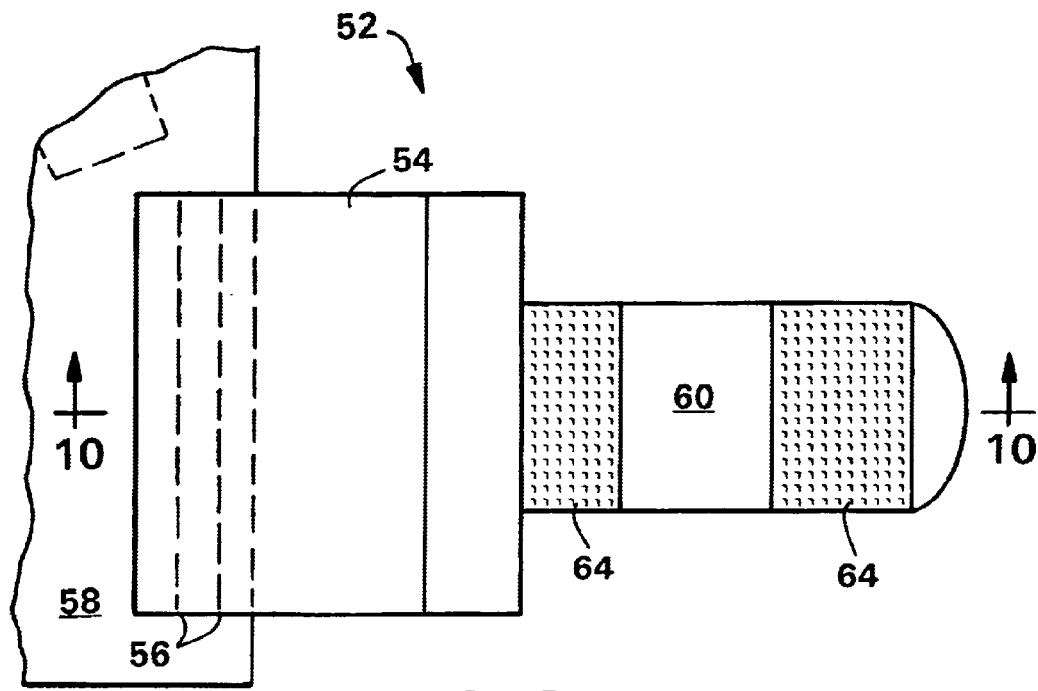
FIG. 9 is a top plan view of one embodiment of a fastening tab according to the present invention.
Figure 10:
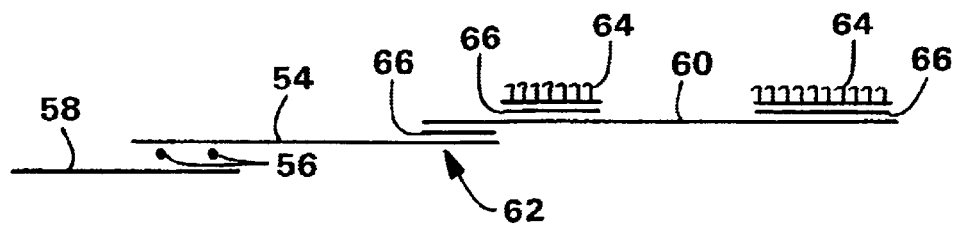
FIG. 10 is a cross-sectional view taken along line 10—10 of FIG. 9.

FIGS. 9–16 illustrate specific embodiments of the fastening tabs according to the present invention. With reference to FIGS. 9 and 10, mechanical fastening tab 52 comprises an elastomeric material 54 which is attached by bond lines 56 to bodyside liner 58. A first substrate 60 is attached to elastomeric material 54 in overlap area 62. Hook material 64 is attached to first substrate 60 by adhesive layers 66. Locating the hook material 64 on the first substrate 60 in an area other than overlap area 62 has been found to increase the flexibility (lower the Gurley stiffness) of the mechanical fastening tab 52.

Figure 11:
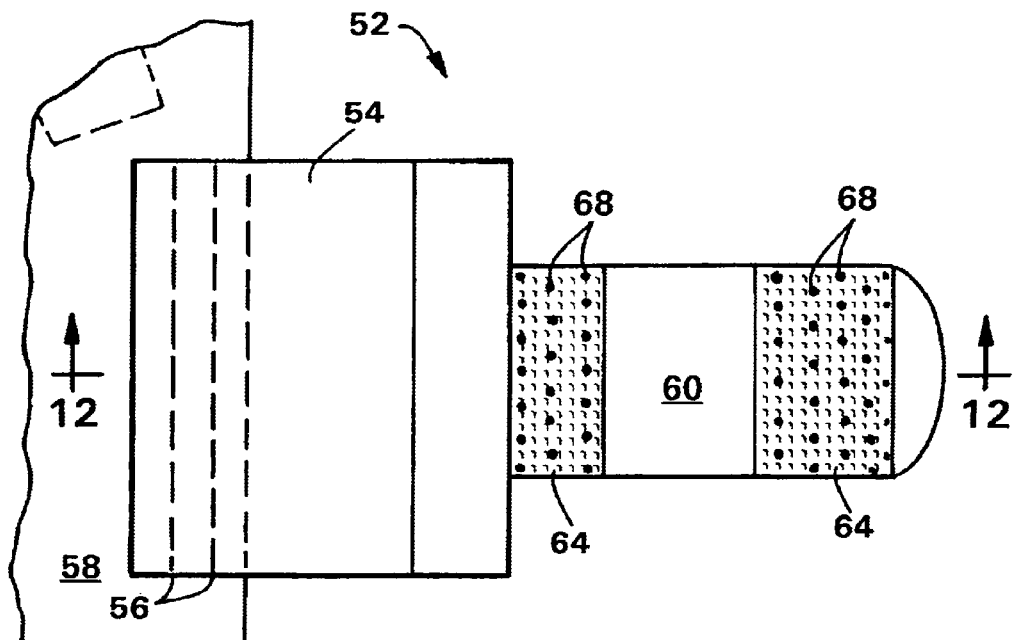
FIG. 11 is a top plan view of one embodiment of a fastening tab according to the present invention.
Figure 12:
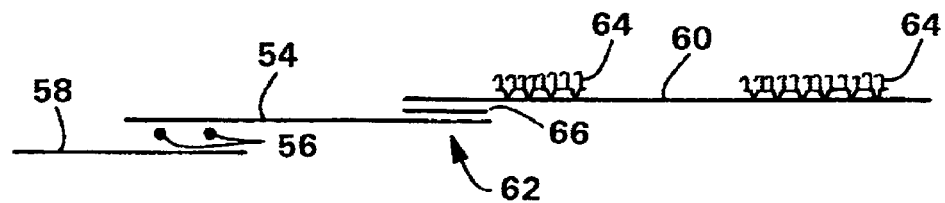
FIG. 12 is a cross-sectional view taken along line 12—12 of FIG. 11.

FIGS. 11 and 12 illustrate an embodiment of the fastening tabs of the present invention similar to those illustrated in FIGS. 9 and 10. Accordingly, like numerals in FIGS. 11 and 12 represent like elements from FIGS. 9 and 10. The fastening tabs illustrated in FIGS. 11 and 12 differ from those illustrated in FIGS. 9 and 10 in that hook materials 64 are thermally bonded to the first substrate 60 at bond points 68. Replacing the adhesive layer 66 illustrated in FIGS. 9 and 10 with the bond points 68 illustrated in FIGS. 11 and 12 has been found to produce a fastening tab which may be more flexible due to the removal of the adhesive layer 66.

Figure 13:
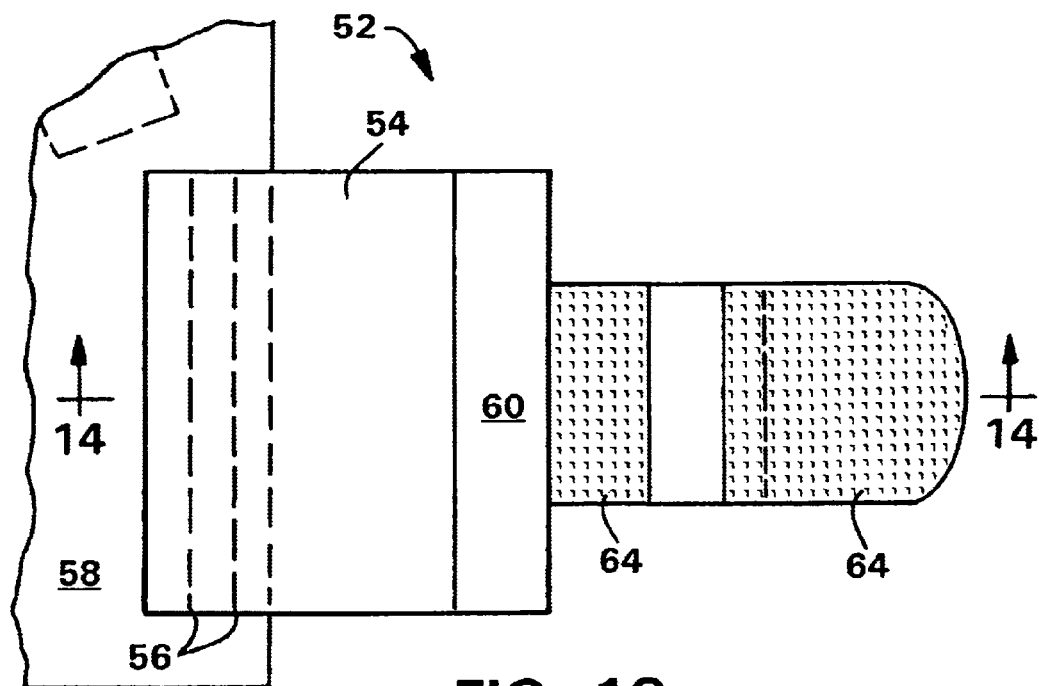
FIG. 13 is a top plan view of one embodiment of a fastening tab according to the present invention.
Figure 14:
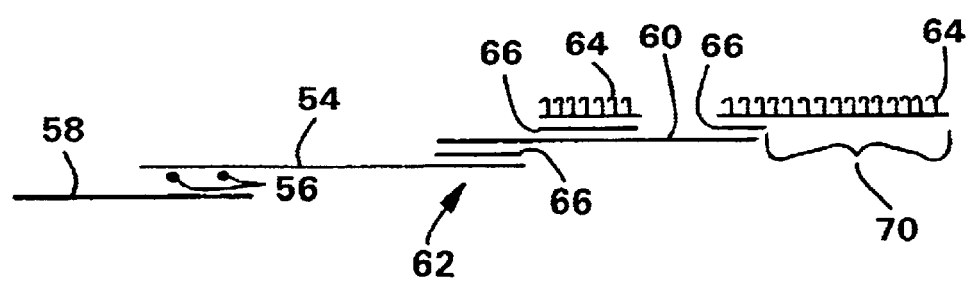
FIG. 14 is a cross-sectional view taken along line 14—14 of FIG. 13.

FIGS. 13 and 14 illustrate another alternative embodiment of fastening tab 52. Again, like numerals appearing in FIGS. 13 and 14 represent like elements appearing in FIGS. 9–12. The fastening tab illustrated in FIGS. 13 and 14 is identical to that illustrated in FIGS. 9 and 10 with the exception that the hook material 64 located on the end of fastening tab 52 opposite that end attached to bodyside liner 58 is not completely overlaid by the first substrate 60. That is, a portion 70 of hook material 64 is not in an overlapping relationship with the first substrate 60. Thus, the portion 70 of fastening tab 52 has an increased flexibility due to the absence of adhesive layer 66 and first substrate 60 in portion 70.

Figure 15:
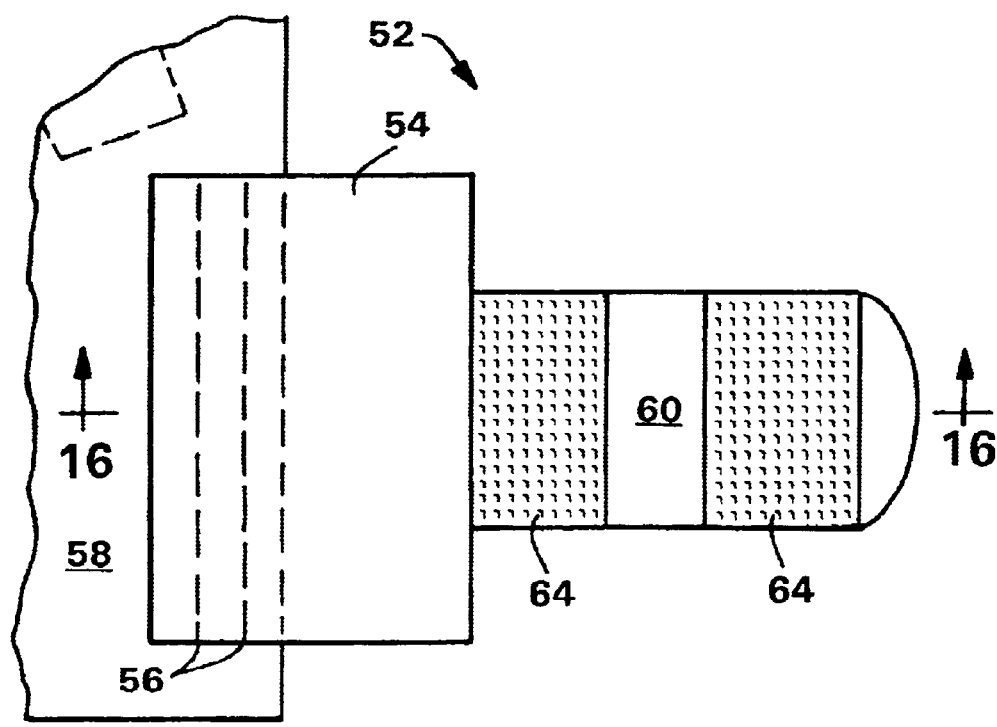
FIG. 15 is a top plan view of one embodiment of a fastening tab according to the present invention.
Figure 16:
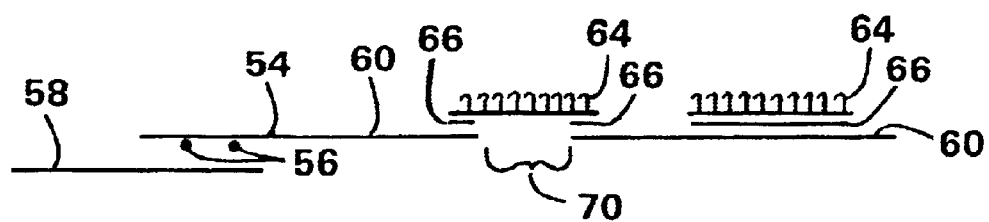
FIG. 16 is a cross-sectional view taken along line 16—16 of FIG. 15.

FIGS. 15 and 16 illustrate a further alternative embodiment of fastening tab 52. Again, like numerals in FIGS. 15 and 16 represent like elements from FIGS. 9–12. The fastening tab illustrated in FIGS. 15 and 16 is similar to that illustrated in FIGS. 13 and 14 with the exception that the first substrate 60 has been divided into two pieces, which pieces are joined to hook materials 64 to define portion 70 of the hook material 64 which is not overlaid by the first substrate 60. This again has been found to increase the flexibility of the fastening tab 52 in that portion 70 which is not overlaid by the first substrate 60.

The fastening tab and hook material may have other alternative shapes and configurations. For example, such shapes and configurations are described in U.S. patent application Ser. No. 08/366,080 filed on even date herewith in the name of Zehner et al. which is hereby incorporated by reference.

Test Methods

Gurley Stiffness

A suitable technique for determining Gurley Stiffness values is set forth in TAPPI Standard Test T 543 om-94 (Stiffness of paper (Gurley type stiffness tester)). A suitable testing apparatus is a Gurley Digital Stiffness Tester: Model 4171-D manufactured by Teledyne Gurley, 514 Fulton Street, Troy, N.Y. 12181-0088. This instrument allows the testing of a wide variety of materials through the use of various lengths and widths in combination with the use of a 5, 25, 50, or 200 gram weight placed in one of three positions on the pointer of the apparatus. For purposes of the present description, the stated Gurley stiffness values are intended to correspond to the values that would be generated by a "standard" sized sample. Accordingly, the scale readings from the Gurley stiffness tester are appropriately converted to the stiffness of a standard size sample and are expressed in terms of milligrams. The standard size sample has a width of 1" and a nominal length of 3" (actual length of 3.5"). The actual length of the sample is the nominal length, plus an additional 0.25" of length for holding in the clamp and another 0.25" of length for overlapping the vane. Tables of factors for taking scale readings generated with non-standard sized test samples and converting the readings to the stiffness of the standard size sample are given in the Instruction Manual for the Gurley Stiffness Tester provided by Teledyne Gurley. Accordingly, other designated dimensions for the test sample may also be conveniently employed so long as the appropriate conversion factor is employed to determine the appropriate value which corresponds to the standard size sample.

EXAMPLES

Example 1

A fastening tab is formed employing a hook material available from Velcro Group Company under the trade designation CFM-22-1056 (also known as HTH-856). The hook material has a hook height (from the top surface of the base film, theoretical values) of 0.028 inch and a hook width (at the widest location, theoretical values) of about 0.008 inch. The hook material has a base film thickness of 0.009–0.012 inch, a hook density of 890 hooks per square inch, and is formed from a polymeric material having a flexural modulus of 110–140 kilo pounds per square inch.

The hook material described above is attached to a neck-bonded-laminate (NBL) material to form a fastening tab. The hook material has a dimension of 1.75 inches by 0.5 inch. The neck-bonded-laminate (NBL) is formed as described in U.S. Pat. No. 5,226,992 issued Jul. 13, 1993, to Morman. The NBL employed included three layers. The outer two layers were polypropylene spunbond layers having a basis weight of 1.4 ounce per square yard and being formed from 2–3 denier fibers. The center layer was an elastomeric film having a basis weight of 45 grams per square meter and being formed from Kraton™ 2740X, a polymeric resin available from Shell Chemical Company. The NBL material has a length of 4 inches and a width of 2.75 inches. The hook material is attached to the NBL material by ultrasonic (about 6.25 percent bond area) and adhesive bonding. A 1.0 ounce per square yard spunbond material (1.0 inch×0.75 inch) is located between the hook material and the NBL material.

Additional fastening tabs are formed in the same manner except that bond lines, such as those illustrated in FIGS. 3 and 4, are formed in the fastening tabs. The bond lines have a width of about 0.5 centimeter and extend across the entire machine direction of the material. Three bond lines were formed on the fastening tab. In one case, the bond lines were registered such that one bond line was located approximately 0.635 centimeter from each end of the hook material (CD direction) and one bond line was located generally in the center of the cross direction length of the hook material (Registered bond lines). In an alternative embodiment three bond lines were formed on each fastening tab, but the bond lines were unregistered so that the location of the bond lines along the cross direction length of the hook material varied (Unregistered bond lines). These hook materials were then subjected to Gurley stiffness testing. The fastening tabs are then used to replace the mechanical fastening tabs supplied on the commercially available HUGGIES® Supreme diaper (Step 4). That is, the non-elastomeric ears of the HUGGIES® Supreme diaper are replaced with the fastening tabs described above.

The diapers thus formed are subjected to sensory use panel testing. In a sensory use panel, mothers are trained and asked to monitor a number of specific attributes during usage of the test diapers. In this particular test, care givers were asked, inter alia, to monitor the degree of hook irritation and the number of pop-opens (unassisted separation of the hook and loop fastening materials). In the sensory use panel test 60 children used each diaper design for 1 week. Thus, each child was involved in the study for a period of 3 weeks. Each child used all three diaper designs (unbonded, registered bond lines and unregistered bond lines).

Each of the three diaper designs was used by 20 children during each week of the three week study. The results of this testing are set forth in Table 1.

TABLE 1

|  | Gurley Stiffness[1] | Number of Diapers | Hook Irritation | Pop-Opens |
|---|---|---|---|---|
| No bond lines | 1818.2* | 1785 | 2.41% | 1.85% |
| Registered bond lines | 98.6 | 1724 | 1.10% | 3.71% |
| Unregistered bond line | 438.7 | 1685 | 1.36% | 2.91% |

*Not an example of the present invention
[1]In milligrams measured in machine direction. (Average of 5 samples.)

As can be seen from Table 1, the presence of both the registered and unregistered bond lines resulted in lower hook irritation. It is also noted that the number of pop-opens increased. This is believed to be the result of a perceived increase in stiffness in the cross machine direction caused by the bond lines. This demonstrates the importance of flexibility in both the machine direction and the cross machine direction and the need to balance flexibility properties to achieve your desired results.

Example 2

The Following Materials Are Subjected to Gurley Stiffness Testing
1. A hook material available from the Minnesota Mining and Manufacturing Company, St. Paul, Minn., under the designation CS-200.
2. A spunbond/meltblown/spunbond material having a basis weight of 1.7 ounces per square yard (57.8 grams per square meter) comprising two outer layers of polypropylene spunbond material having a basis weight of 21.25 grams per square meter. The middle layer comprises polypropylene meltblown fibers having a basis weight of 15.3 grams per square meter.
3. A stretch thermal laminate material comprising a 0.6 mil (0.015 millimeter) polypropylene blown film and 0.7 ounce per square yard (23.6 grams per square meter) polypropylene spunbond material. The spunbond material is composed of about 2.0 denier fibers. The stretch thermal laminate is formed by stretching the polypropylene film, in one direction, until it is extended by 25 percent. The spunbond polypropylene is then brought into face-to-face contact with the stretched polypropylene film. The polypropylene film and spunbond material are then thermally bonded together at spaced intervals. The resulting laminate has a plurality of separate and distinct bond sites with an overall bond area of about 13 percent per unit area. After the film and spunbond material are laminated to one another, the laminate is allowed to relax. The film layer retracts about 10 percent, thereby leaving the film permanently deformed to a length of about 15 percent greater than its original length.
4. A knit loop material commercially available from Guilford Mills under the trade designation Style 34285.

5. A laminate of material 1 with material 2. The laminate is through the use of double-sided adhesive tape such as that available from the Minnesota Mining and Manufacturing Company under the designation #465. Sufficient double sided tape is used to cover the facing surfaces of the two materials.
6. The laminate which is material 5 mechanically engaged with material 3. The laminate was mechanically engaged with material 3 with a standard 4.5 lb mechanical roller (available from Chemsultants International located in Mentor, Ohio) by rolling the roller across the materials (in a facing relationship) once in each direction.
7. A laminate of material 4 on material 3. The laminate was form as described above in connection with material 5.
8. Material 1 mechanically engaged with material 3. The materials were mechanically engaged as described in connection with material 6.
9. A laminate of material 3 with material 2 which was then mechanically engaged with material 1. The laminate was formed and mechanically engaged as described above in connection with material 5 and material 6.

The results of the Gurley stiffness testing are set forth in Table 2. The data set forth in Table 2 represents an average of 10 test repetitions.

TABLE 2

| Material | Test Direction[1] | Gurley Stiffness[2] | Std. Deviation |
|---|---|---|---|
| 1 | MD | 16.87 | 2.05 |
| 1 | CD | 16.54 | 1.71 |
| 2 | MD | 8.60 | 1.7 |
| 2 | CD | 29.69 | 8.51 |
| 3 | MD | 4.77 | 1.31 |
| 3 | CD | 6.49 | 5.79 |
| 4 | MD | 5.44 | 3.29 |
| 4 | CD | 1.39 | 0.47 |
| 5 | MD | 98.3 | 22.3 |
| 5 | CD | 185.2 | 24.7 |
| 6 | MD | 267.4 | 36.2 |
| 6 | CD | 391.9 | 53.9 |
| 7 | MD | 28.7 | 5.3 |
| 7 | CD | 37.5 | 6.7 |
| 8 | MD | 103.2 | 18.2 |
| 8 | CD | 122.5 | 33.5 |
| 9 | MD | 314.1 | 28.7 |
| 9 | CD | 335.2 | 52.5 |

[1]MD = Machine Direction; CD = Cross Direction
[2]In milligrams

Example 3

The following material was subjected to tensile testing in a manner similar to that described in American Society of Testing and Materials (ASTM) Test Method D-882:

A laminate of a bonded carded web and a film. The bonded carded web is formed from polypropylene fibers available from Hercules Inc, under the designation T-196. The bonded carded web has a basis weight of 0.77 ounce per square yard (26 grams per square meter). The bonded carded web is adhesively laminated to a breathable film available from The Sam Woo Corporation. The film has a basis weight of 39 grams per square meter. The film was formed from about 26 weight percent linear low density polyethylene, about 10 weight percent high density polyethylene, about 10 weight percent ethylene vinyl acetate, about 48 weight percent of calcium carbonate coated with a fatty acid and about 6 weight percent of other additives. The laminate was tested to determine both the MD and CD tensile strength. The results of this testing are set forth in Table 3.

TABLE 3

| Direction | Peak Load | Std. Deviation | Peak Strain | Std. Deviation |
|---|---|---|---|---|
| CD | 759.3 | 45.6 | 269.0 | 138.1 |
| MD | 3704.2 | 295.7 | 39.4 | 3.8 |

All values are in grams force.
Peak Load and Peak Strain values represent the average of 6 repetitions The laminate described above and a hook material available from the Minnesota Mining and Manufacturing Company under the designation CS-200 were subjected to shear testing generally as outlined in ASTM test method D-5169. The result of this testing are set forth in Table 4.

TABLE 4

| Direction[1] | Peak Load[2] | Std. Deviation | Total Energy[3] | Std. Deviation |
|---|---|---|---|---|
| MD | 1377.5 | 695.8 | 0.2212 | 0.1343 |
| CD | 814.13 | 44.67 | 2.29 | 1.16 |

[1]Direction shear forces applied to laminate material.
[2]In grams force
[3]Tensile Energy Absorbed (TEA) at Peak, in Inch-Pounds per square Inch. Refers to total area under stress/strain curve, to peak, generated during shear testing.

As can be seen from the above data, the ability of the laminate material to deform during application of shear forces greatly increases the total shear energy which can be applied to the system before failure of the bond between the hook material and the laminate.

While the present invention has been described in terms of the specific embodiments set forth herein, those skilled in the art will recognize numerous variations and alterations thereof which are intended to be within the scope of the claims appended hereto.

What is claimed is:

1. A mechanical fastening tab for use on a disposable absorbent product, said fastening tab comprising:
   a substrate adapted to be joined to said disposable absorbent product; and
   a first mechanical fastener component joined to said substrate, said first mechanical fastener component being adapted to releasably engage a second mechanical fastener component, said fastening tab having a Gurley stiffness value of less than about 200 milligrams in an area of said fastening tab including said first mechanical fastener component.

2. The mechanical fastening tab according to claim 1 wherein said first mechanical fastener component is a hook material.

3. The mechanical fastening tab according to claim 1 wherein said Gurley stiffness value is determined in the machine direction of the mechanical fastening tab.

4. The mechanical fastening tab according to claim 1 wherein said substrate overlays 100 percent of a planar surface of said first mechanical fastener component.

5. The mechanical fastening tab according to claim 1 wherein said substrate overlays from about 2 to about 98 percent of a planar surface of said first mechanical fastener component.

6. The mechanical fastening tab according to claim 1 wherein said first mechanical fastener component is formed from a polymeric material having a flexural modulus of greater than about 100 kpsi.

7. A mechanical fastening tab according to claim 1 wherein said first mechanical fastener component is formed from a polymeric material having a flexural modulus of from about 50 kpsi to about 300 kpsi.

8. The mechanical fastening tab according to claim 1 wherein said fastening tab comprises an elastomeric material.

9. A disposable product, said disposable product comprising:
   an outer cover; and
   a mechanical fastening tab, said mechanical fastening tab comprising:
   a substrate joined to said disposable product; and
   a first mechanical fastener component joined to said substrate, said first mechanical fastener component being adapted to releasably engage with said outer cover, said fastening tab having a Gurley stiffness value of less than about 200 milligrams in an area of said fastening tab including said first mechanical fastener component.

10. The disposable product according to claim 9 wherein said fastening tab has a Gurley stiffness value of less than about 75 milligrams.

11. The disposable product according to claim 9 wherein when said first mechanical fastener component is releasably engaged with said outer cover and is subjected to shear forces, said outer cover deforms to dissipate a portion of said shear forces.

12. The disposable product according to claim 9 further comprising a bodyside liner and an absorbent core located between said outer cover and said bodyside liner.

13. The disposable product according to claim 9 wherein said substrate overlays 100 percent of a planar surface of said first mechanical fastener component.

14. The disposable product according to claim 9 wherein said substrate overlays from about 98 to about 2 percent of a planar surface of said first mechanical fastener component.

15. The disposable product according to claim 9 wherein said outer cover comprises a nonwoven outer surface.

16. The disposable product according to claim 15 wherein said outer cover comprises a film/nonwoven laminate.

17. The disposable product according to claim 15 wherein said outer cover has a Gurley stiffness value of less than about 100 milligrams.

18. The disposable product according to claim 15 wherein said outer cover has a Gurley stiffness value of less than about 75 milligrams.

19. The disposable product according to claim 15 wherein said outer cover has a Gurley stiffness value of less than about 50 milligrams.

20. The disposable product according to claim 9 wherein said outer cover further comprises a second mechanical fastener component.

21. The disposable product according to claim 20 wherein said second mechanical fastener component comprises a loop material.

22. The disposable product according to claim 21 wherein said loop material is selected from the group consisting of woven materials, nonwoven materials, and knit materials.

23. The disposable product according to claim 9 wherein said fastening tab comprises an elastomeric material.

24. A disposable product, said disposable product comprising:
   an outer cover; and
   a mechanical fastening tab, said mechanical fastening tab comprising:
   a substrate joined to said disposable product; and
   a first mechanical fastener component joined to said substrate, said first mechanical fastener component being adapted to releasably engage with said outer cover, said fastening tab having a Gurley stiffness value of less than about 1000 milligrams in an area of said fastening tab including said first mechanical fastener component, and wherein when said fastening tab and said outer cover are engaged to form a fastener composite, said fastener composite has a Gurley stiffness values of less than 200 milligrams.

25. The disposable product according to claim 24 wherein said fastener composite has a Gurley stiffness values of less than 75 milligrams.

26. A disposable absorbent product, said disposable absorbent product comprising:
   an outer cover comprising a film material having attached thereto a nonwoven material to form a laminate, said laminate having a Gurley stiffness value of less than 100 milligrams;
   a bodyside liner;
   an absorbent core located between said outer cover and said bodyside liner; and
   a mechanical fastening tab, said mechanical fastening tab comprising;
   a substrate joined to said disposable absorbent product; and
   a first mechanical fastener component joined to said substrate, said first mechanical fastener component being adapted to releasably engage with said laminate, said fastening tab having a Gurley stiffness value of less than about 200 milligrams in an area of said fastening tab including said first mechanical fastener component.

27. The disposable absorbent product according to claim 26 wherein said fastening tab has a Gurley stiffness value of less than about 75 milligrams.

28. The disposable absorbent product according to claim 26 wherein said first mechanical fastener component is a hook material.

29. The disposable absorbent product according to claim 26 wherein said laminate has a Gurley stiffness value of less than 75 milligrams.

30. The disposable absorbent product according to claim 26 wherein said laminate has a Gurley stiffness value of less than 50 milligrams.

31. A disposable absorbent product, said disposable absorbent product comprising:
   an outer cover comprising a film material having attached thereto a nonwoven material to form a laminate, said laminate having a Gurley stiffness value of less than 100 milligrams;
   a bodyside liner;
   an absorbent core located between said outer cover and said bodyside liner; and
   a mechanical fastening tab, said mechanical fastening tab comprising:
   a substrate joined to said disposable absorbent product; and
   a first mechanical fastener component joined to said substrate, said first mechanical fastener component being adapted to releasably engage with said laminate, said fastening tab having a Gurley stiffness value of less than about 1000 milligrams in an area of said fastening tab including said first mechanical fastener component and wherein when said fastening tab and said laminate are engaged to form a fastener composite, said fastener composite has a Gurley stiffness value of less than 500 milligrams.

32. The disposable absorbent product according to claim 31 wherein said fastener composite has a Gurley stiffness value of less than 200 milligrams.

33. The disposable absorbent product according to claim 31 wherein said fastener composite has a Gurley stiffness value of less than 75 milligrams.

34. A disposable absorbent product, said disposable absorbent product comprising:
- an outer cover comprising a film material having attached thereto a nonwoven material to form a laminate, the nonwoven material forming the outer surface of said laminate, said laminate having a Gurley stiffness value of less than 100 milligrams;
- a bodyside liner;
- an absorbent core located between said outer cover and said bodyside liner; and
- a mechanical fastening tab, said mechanical fastening tab comprising:
  - a substrate joined to said disposable absorbent product; and
  - a first mechanical fastener component joined to said substrate, said first mechanical fastener component being adapted to releasably engage with said nonwoven material of said laminate, said fastening tab having a Gurley stiffness value of less than about 200 milligrams in an area of said fastening tab including said first mechanical fastener component wherein when said first mechanical fastener component is releasably engaged with said nonwoven material of said laminate and is subjected to shear forces, said laminate deforms to dissipate a portion of said shear forces.

35. The disposable absorbent product according to claim 34 wherein said fastening tab has a Gurley stiffness value of less than about 75 milligrams.

36. The disposable absorbent product according to claim 34 wherein said first mechanical fastener component is a hook material.

37. The disposable absorbent product according to claim 34 wherein said laminate has a Gurley stiffness value of less than 75 milligrams.

38. The disposable absorbent product according to claim 34 wherein said laminate has a Gurley stiffness value of less than 50 milligrams.

39. The disposable absorbent product according to claim 34 wherein said outer cover is a stretch thermal laminate.

40. The disposable absorbent product according to claim 34 wherein said outer cover is an elastomeric material.

41. A mechanical fastening tab for use on a disposable absorbent product, said fastening tab comprising:
- a substrate adapted to be joined to said disposable absorbent product; and
- a first mechanical fastener component joined to said substrate, said first mechanical fastener component being adapted to releasably engage a second mechanical fastener component, said fastening tab having a Gurley stiffness value of less than about 75 milligrams in an area of said fastening tab including said first mechanical fastener component.

42. A disposable product, said disposable product comprising:
- an outer cover;
- a bodyside liner and an absorbent core located between said outer cover and said bodyside liner, the product having a machine direction corresponding to its length and a cross-machine direction perpendicular to the machine direction;
- a mechanical fastening tab, said fastening tab comprising a substrate joined to said disposable absorbent product, and a first mechanical fastener component joined to said substrate;
- said outer cover comprising a second mechanical fastener component, and said first mechanical fastener component being adapted to releasably engage the second mechanical fastener component;
- wherein said fastening tab has a Gurley stiffness value of less than about 200 milligrams in both the machine and cross-machine directions in an area of said fastening tab including said first mechanical fastening component; and
- wherein when said fastening tab and said outer cover are engaged to form a fastener composite, said fastener composite has a Gurley stiffness value of less than 500 milligrams.

* * * * *